US009408576B2

(12) United States Patent
Chon et al.

(10) Patent No.: US 9,408,576 B2
(45) Date of Patent: *Aug. 9, 2016

(54) DETECTION AND MONITORING OF ATRIAL FIBRILLATION

(71) Applicant: Worcester Polytechnic Institute, Worcester, MA (US)

(72) Inventors: Ki H. Chon, Worcester, MA (US); Jowoon Chong, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 11 days.

This patent is subject to a terminal disclaimer.

(21) Appl. No.: 14/267,177

(22) Filed: May 1, 2014

(65) Prior Publication Data

US 2014/0330134 A1 Nov. 6, 2014

Related U.S. Application Data

(60) Provisional application No. 61/818,207, filed on May 1, 2013.

(51) Int. Cl.
*A61B 5/00* (2006.01)
*A61B 5/024* (2006.01)
*A61B 5/046* (2006.01)

(52) U.S. Cl.
CPC ............ *A61B 5/7282* (2013.01); *A61B 5/02416* (2013.01); *A61B 5/046* (2013.01); *A61B 5/6898* (2013.01); *A61B 5/02438* (2013.01); *A61B 5/7264* (2013.01)

(58) Field of Classification Search
CPC ........... A61B 5/02416; A61B 5/02438; A61B 5/046; A61B 5/6898; A61B 5/7264
See application file for complete search history.

(56) References Cited

U.S. PATENT DOCUMENTS

| 5,682,901 | A | 11/1997 | Kamen | |
|---|---|---|---|---|
| 6,392,584 | B1* | 5/2002 | Eklund | G01H 1/003 341/183 |
| 7,623,911 | B2* | 11/2009 | Sarkar | A61B 5/0464 600/510 |
| 2004/0230105 | A1* | 11/2004 | Geva | A61B 5/04012 600/301 |
| 2007/0032733 | A1* | 2/2007 | Burton | A61B 5/02405 600/509 |
| 2010/0191130 | A1* | 7/2010 | Glass | A61B 5/0456 600/509 |
| 2011/0152957 | A1* | 6/2011 | Shaquer | A61B 5/046 607/5 |
| 2011/0166466 | A1* | 7/2011 | Chon | A61B 5/046 600/513 |
| 2011/0208079 | A1 | 8/2011 | Babaeizadeh et al. | |

(Continued)

OTHER PUBLICATIONS

Selvaraj, N. et al. "Statistical Approach for the Detection of Motion/Noise Artifacts in Photoplethysmogram." Annual International Conference of the IEEE Engineering in Medicine and Biology Society, Aug. 30-Sep. 3, 2011:4972-4975.

(Continued)

*Primary Examiner* — Baisakhi Roy
(74) *Attorney, Agent, or Firm* — Burns & Levinson LLP; Orlando Lopez

(57) ABSTRACT

Enhanced real-time realizable AF algorithm for accurate detection of, and discrimination between, NSR, AF, PVC, and PAC. The method of these teachings includes an AF detection method having a modified Poincare approach in order to differentiate various patterns of PAC and PVC from NSR and AF. The method of these teachings can also apply to the Kullback-Leibler divergence or the Turning Point Ratio (TPR) to differentiate between various patterns of PAC and PVC from NSR and AF.

20 Claims, 16 Drawing Sheets

(56) References Cited

U.S. PATENT DOCUMENTS

2013/0102864 A1     4/2013   Sacco et al.
2014/0296655 A1*   10/2014   Akhbardeh .......... A61B 5/4824
                                                                              600/301

OTHER PUBLICATIONS

Sarkar, S. et al. "A detector for a chronic implantable atrial tachyarrhythmia monitor." IEEE Trans Biomed Eng. Mar. 2008; 55(3):1219-24.

Yang, A. C-C. (2006) "Poincaré Plots: A Mini Review." Downloaded from www.physionet.org/events/hrv-2006/yang.pdf.

Piskorski, J. et al. "Filtering Poincaré plots." Computational methods in science and technology Jan. 2005; 11(1):39-48.

McManus, D.D. et al. "A Novel Application for the Detection of an Irregular Pulse using an iPhone 4S in Patients with Atrial Fibrillation." Heart Rhythm. Mar. 2013; 10(3):315-319.

International Search Report and Written Opinion dated Aug. 26, 2014 for PCT/US14/36329.

* cited by examiner

DETECTION AND MONITORING OF ATRIAL FIBRILLATION

CROSS REFERENCE TO RELATED APPLICATIONS

This application claims priority of U.S. Provisional Application No. 61/818,207, entitled DETECTION AND MONITORING OF ATRIAL FIBRILLATION, filed on May 1, 2013, which is incorporated by reference herein is entirety and for all purposes.

STATEMENT REGARDING FEDERALLY SPONSORED RESEARCH OR DEVELOPMENT

This invention was made partially with U.S. Government support from the United States Army under grant #215700. The U.S. Government has certain rights in the invention.

BACKGROUND

These teachings relate generally to methods and systems for detection and monitoring of Atrial Fibrillation (AF).

The prevalence of AF is increasing (20.7 per 1,000 patient years (2)), especially among the growing number of older Americans. At age 55, the lifetime risk for developing AF is approximately 1 in 5 and it is estimated that 16 million individuals may be affected by 2040. The growing population burden of AF has widespread clinical and public health relevance, since AF is closely linked to increased risk for stroke and heart failure, as well as diminished quality of life and longevity. Novel treatments for AF, such as catheter-based ablation, exist but require post-treatment monitoring to establish treatment response. To date, traditional methods of AF detection have been confounded by the often paroxysmal and minimally symptomatic nature of this arrhythmia. Brief, asymptomatic episodes of AF remain associated with increased morbidity and mortality, highlighting the need for sensitive AF screening instruments that do not rely on patient symptoms. Contemporary screening for AF involves the use of continuous ambulatory electrocardiographic monitoring (Holter) or longer-duration symptom-triggered (Event) monitors. The detection of arrhythmias via a smartphone application, on the other hand, could lead to many people self-screening even if asymptomatic, if there was sufficient publicity about the dangers of AF and the application was widely adopted. Certainly the barriers to adoption are very low, as most people perceive using the application as fun, which no one has ever claimed about wearing a Holter monitor. Although monitors with automated AF detection capabilities are increasingly utilized to screen for serious atrial arrhythmias, especially after AF ablation, they are severely limited by motion and noise artifacts and an inability to discriminate between AF and other atrial arrhythmias. The ideal AF detection tool would provide real-time, automatic detection of AF in a sensitive and specific manner. Furthermore, since AF is often associated with the clinically relevant, but distinct, premature beats (PVC and PAC), the ideal AF screening instrument would also be able to recognize PVC and PAC.

Atrial Fibrillation (AF) is the most common sustained dysrhythmia worldwide. Over 2.3 million Americans are currently diagnosed, and the prevalence of AF is increasing with the aging of the U.S. population. Through its association with increased risk for heart failure, stroke, hospitalization and mortality, AF has a profound impact on the longevity and quality of life of a growing number of Americans. Although new AF treatment strategies have emerged over the last decade, a major challenge facing clinicians and researchers is the paroxysmal, often short-lived, and sometimes asymptomatic nature of AF.

Although the population with undiagnosed AF is substantial, studies have shown that more frequent monitoring can improve AF detection. There is therefore a pressing need to develop methods for accurate AF detection and monitoring in order to improve patient care and reduce healthcare costs associated with treating complications from AF. Such a method would have important clinical and research applications for AF screening as well as for assessing treatment response (e.g. after cardioversion or AF ablation). For these reasons, the importance of developing new AF detection technologies was emphasized by a recent NHLBI Expert panel.

Since the standard-of-care for detection of AF relies on the arrhythmia being present during an electrocardiogram (ECG), a great deal of serendipity is required in the diagnosis of this often intermittent arrhythmia. A more effective AF detection strategy requires a readily available and cost-effective monitoring device that could be operated by a patient on a daily basis, combined with an accurate, real-time AF detection algorithm. The ideal AF monitoring device would be accessible, inexpensive, and simple to operate in order to be widely accepted by individuals with, or at risk for, AF.

A smartphone application to measure heart interval series and then use this data to detect AF real-time was previously developed. That approach uses standard phone components and does not require extra hardware, as the optical video monitoring of the skin with the standard digital camera embedded in smartphones is sufficient to detect variability in the heart rate signal (see FIG. 8), indicating that accurate pulse interval data can be obtained. A set of statistical algorithms has been developed that can accurately identify AF using signatures of near-random characteristics in the pulse intervals. That AF detection method is real-time realizable and has demonstrated a sensitivity of 94.4% and specificity of 95.1% for detection of AF beats using data from the MIT-BIH AF database. For clinical applications, however, it is enough to detect AF episodes, and an episode detection rate of 100% has been achieved. In a recent prospective clinical investigation involving 76 participants with AF, it was demonstrated that the smartphone-based AF detection approach discriminated AF from normal sinus rhythm. Although that algorithm is robust for AF detection, a major limitation is that it is not designed to discriminate premature ventricular contractions (PVC) and premature atrial contractions (PAC) from AF. Consequently, that AF algorithm has resulted in false detection of AF in the presence of many PAC/PVC episodes interspersed with normal sinus rhythm (NSR) because the presence of many PAC/PVC episodes interspersed with NSR can mimic the random dynamics of the AF.

There is a need to enhance the real-time realizable AF algorithm for accurate detection of, and discrimination between, NSR, AF, PVC, and PAC.

BRIEF SUMMARY

Enhanced real-time realizable AF algorithm for accurate detection of, and discrimination between, NSR, AF, PVC, and PAC are disclosed herein below.

In one or more embodiments, the method of these teachings includes an AF detection method having a modified Poincare approach in order to differentiate various patterns of PAC and PVC from NSR and AF.

In one or more other embodiments, the method of these teachings applies the Kullback-Leibler divergence to differentiate between PVC and PAC.

For a better understanding of the present teachings, together with other and further objects thereof, reference is made to the accompanying drawings and detailed description and its scope will be pointed out in the appended claims.

DETAILED DESCRIPTION

Figure 1:
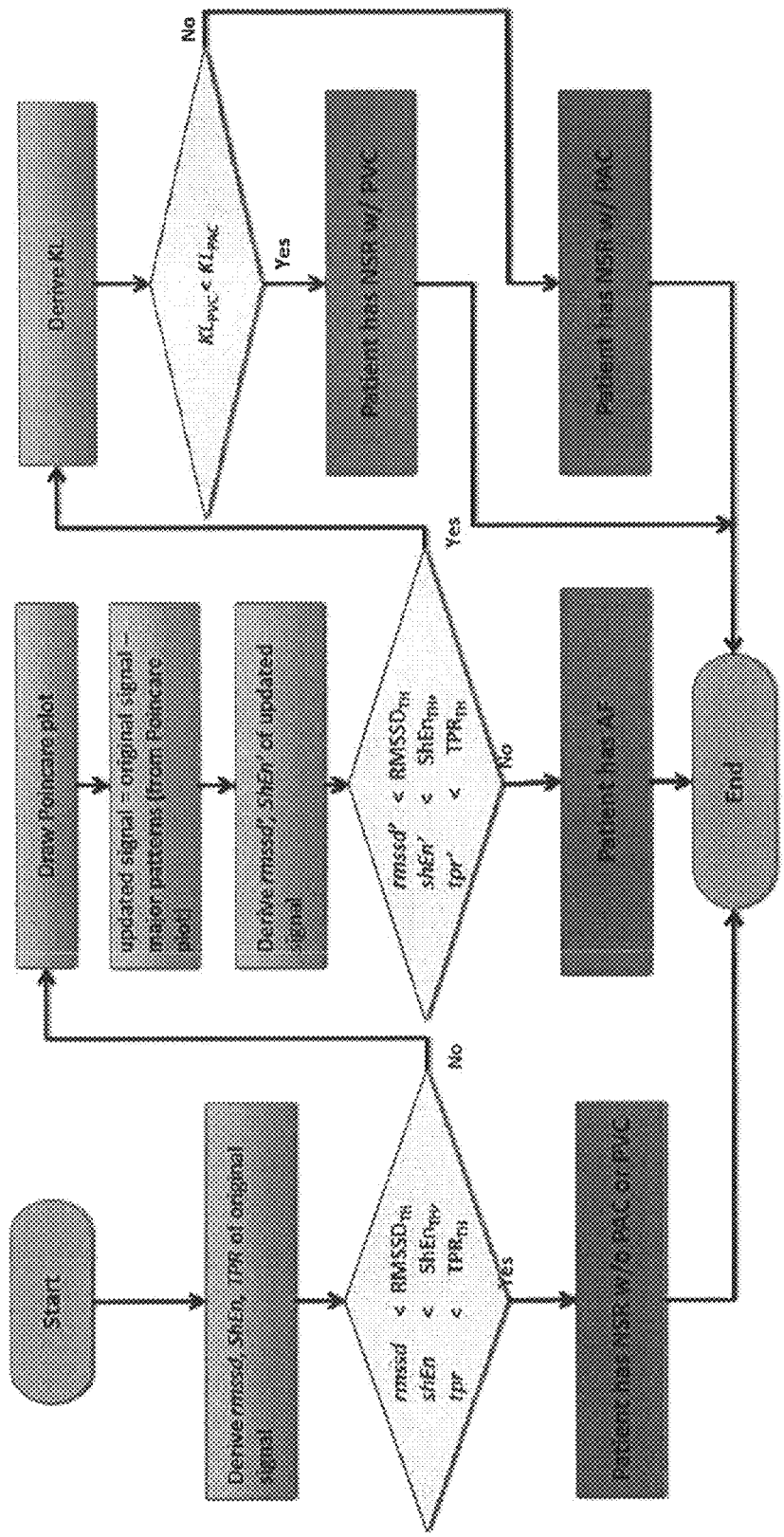
FIG. 1 is a Flowchart of NSR, AF, PVC, PAC detection and discrimination procedures.

The following detailed description presents the currently contemplated modes of carrying out the invention. The description is not to be taken in a limiting sense, but is made merely for the purpose of illustrating the general principles of the invention, since the scope of the invention is best defined by the appended claims.

Current AF algorithms: A number of algorithms have been developed to detect AF and can be categorized as being based on 1) P-wave detection or 2) RR interval (RRI) variability. Since there is no uniform depolarization of the atria during AF, there is no discernible P-wave in the ECG. This fact has been utilized in detection of AF by trying to identify whether the P-wave is absent. However, in most cases the location of the P-wave fiducial point is very difficult to find and often corrupted by noise that is inherent in surface measurements. The methods in the second category do not require identification of the P-wave and are based on the variability of RRI series. However, few algorithms in this category show high predictive value for clinical application. A notable exception includes an algorithm which compares the density histogram of the test RRI (and $\Delta RRI$) segment with previously-compiled standard density histograms of RR (and $\Delta RR$) segments during AF using the Kolmogorov-Smirnov test (16). The inventors reported a sensitivity of 94.4% and specificity of 97.2% for AF beats in the MIT-BIH AF database (16). Similar accuracy was reported by Sarkar et al. using a Lorenz plot between $\Delta RR(i-1)$ and $\Delta RR(i)$ (15), which is incorporated into the Reveal XT product. It should be noted that the accuracy of these 2 methods rely on the robustness of the training data (15, 16). An AF detection algorithm based on statistical analysis of RRI has been recently developed and has been found to produce similar accuracy (8) (see also US Patent application Publication 20110166466, "RR INTERVAL MONITORING METHOD AND BLOOD PRESSURE CUFF UTILIZING SAME," issued as U.S. Pat. No. 8,417,326, and WIPO Publication of International Application No.: PCT/US12/66626, TIME-VARYING COHERENCE FUNCTION FOR ATRIAL FIBRILLATION DETECTION, and corresponding US Patent Application Publication 2013-0144180, all of which are incorporated by reference herein in its entirety and for all purposes). The main advantage of that approach is that it is computationally fast (<0.08 ms per 2 minutes of data) and requires storage of only 3 threshold values. Note that the algorithms by Tateno and Glass, and Sarkar et al., require storage of large amounts of histogram data and threshold values of various characteristics of AF. Importantly, none of the AF detection algorithm described herein above has been proven capable of diagnosing AF and differentiating AF from PAC and PVC or of doing so using standard smart-phone technologies (memory, processor, illumination, and camera).

Current PVC and PAC algorithms: From an algorithmic development perspective, automatic detection of PVCs and PACs is difficult because premature beats often occur infrequently and can be random, leading to false positive AF detection. Premature atrial contractions are generated when a region of the atria other than the sinoatrial node fires early, leading to premature activation of the atria and ventricles. Although spontaneous left atrial/pulmonary vein activity has been shown to trigger AF in some individuals, the link between PACs and risk for AF remains unclear. Premature ventricular contractions occur when a region below the atrioventricular node spontaneously depolarizes, leading to ventricular activation. Both PACs and PVCs can cause symptoms of palpitations very similar to AF, but, as opposed to AF, the clinical course of affected patients is typically benign. Last, PACs and PVCs occur in patterns, specifically occurring every 2nd, 3rd, or 4th beat, termed bigeminy, trigeminy, and quadrigeminy, or combinations of the three.

The presence of many PAC and PVC episodes interspersed among NSR can alter the cardiac signal's dynamics, even mimicking the characteristics of AF. This is because the presence of either PAC or PVC increases the variability in the pulse interval, resulting in more random-like behavior than a segment of data with only NSR. It has been observed that in a 60-beat segment, three or more episodes of PVC, PAC or a combination of the two does result in incorrect detection of AF using an AF detection algorithm. In some patients, therefore, the prevalence of PAC/PVC causes false detection of AF using AF detection algorithm as shown in the Preliminary Results section. Hence, there is a need for developing a new algorithm for detection of PAC/PVC from a pulse interval signal derived from a smartphone.

The most widely-used algorithm for PAC and PVC detection from an ECG signal is based on template matching of PAC/PVC episodes. The main limitation of this approach is that many templates of PAC/PVC waveforms need to be stored in memory and they are compared beat-by-beat to the ECG signal. This approach is clearly only suited for offline computer analysis, not for applications for real time analysis, such as, but not limited to, smartphone applications. These teachings consider a real-time realizable and more efficient method for detection of PAC/PVC than the template matching approach.

The AF detection algorithm of Dash S, Chon K H, Lu S, Raeder E A

As stated in Dash S, Chon K H, Lu S, Raeder E A. Automatic real time detection of atrial fibrillation. Ann Biomed Eng. 2009; 37(9):1701-9, the algorithm includes:

AF Detection Algorithm:

Step 1: Root Mean Square of Successive Differences (RMSSD) was calculated using the following formula:

$$RMSSD = \left(\frac{1}{l-1}\sum_{j=1}^{l-1}(a(j+1)-a(j))^2\right)^{\frac{1}{2}} \quad (1)$$

We divide the RMSSD value by the mean RRI in order to account for the beat-beat variations in HR. This ratio is then compared to a threshold (RmsThresh).

Step 2: Turning Point Ratio (TPR) is based on the nonparametric "Runs Test" used to measure the degree of randomness in a particular time-series. Each beat in a RRI segment is compared to its 2 nearest neighbors and is designated a Turning Point (TP) if it is greater or less than both. The expected number of TP's in a segment of length l is given by $$\mu_{TP} = \frac{2l-4}{3} \quad (2)$$

$$\sigma_{TP} = \sqrt{\frac{16l-29}{90}} \quad (3)$$

A beat segment is considered random if the number of turning points (or TPR, if it is normalized against the length l) falls within some threshold confidence interval (TprThresh) of the expected TPR.

Step 3: Shannon Entropy (SE) is a metric used to measure the level of uncertainty in a random variable by quantifying the probability that runs of patterns exhibiting regularity over some duration of data exhibit similar patters over the next duration of data. It is calculated from a histogram of RR intervals in a segment of length l using 16 equally spaced bins. We can define a probability distribution for the RRI segment using:

$$p(i) = \frac{N_{bin(i)}}{l - N_{outliers}} \quad (4)$$

Here, $N_{bin(i)}$ is the number of beats in the ith bin and $N_{outlier}$ is the number of outliers (16 in or case) and p(t) is the probability associated with all beats falling in the ith bin. The SE is then calculated as $$SE = -\sum_{i=1}^{16}\frac{p(i)\log(p(i))}{\log\left(\frac{1}{16}\right)} \quad (5)$$

The SE is compared to a threshold (SeThresh) to be derived after tuning using the ROC curve.

Step 4: After all the above statistics are calculated, a simple AND condition is applied. The beat segment is considered AF only if all the above statistics cross their respective thresholds.

The SE (also referred to as ShE) quantifies the regularity of pattern in a time series and ShE on the time series $a_i, \ldots, a_{i+L-1}$ is derived as:

$$ShE(a_i, \ldots, a_{i+L-1}) = -\sum_{k=1}^{N_{BIN}}\frac{p(a_i, \ldots, a_{i+L-1},k)\log p(a_i, \ldots a_{i+L-1},k)}{\log(1/N_{BIN})}$$

where $N_{BIN}$ denotes the number of bins, of which each has lower ($B_{LOW,k}$) and upper ($B_{UP,k}$) bin boundaries for $k \in \{1, N_{BIN}\}$ and $p(a_i, \ldots a_{i+L-1},k)$ is expressed as:

$$p(a_i, \ldots, a_{i+L-1}, k) = \sum_{j=0}^{L-1} U(a_{i+j}, k)/(L - N_{outliers})$$

for $$U(a_{i+j}, k) = \begin{cases} 1, & B_{LOW,k} < a_{i+j} < B_{UP,k} \\ 0, & \text{otherwise} \end{cases}$$

The SE of NSR is expected to be small compared to those of AF, PAC and PVC. The TPR is to measure a degree of independence in a time-series. A turning point (TP) is usually defined as a point having larger or smaller value than two nearest neighbor points. The TPRs of NSR and AF are expected to be within in a range since they are from random RRIs while those of PAC and PVC are expected to be out of the range due to their regularities.

Motion and noise artifact detection algorithms: Clinicians have cited motion and noise artifacts in ambulatory monitoring devices as the most common cause of false positive arrhythmia detection, loss of key electrocardiographic data, and inaccurate readings. Numerous efforts have been made, but motion and noise artifacts remain a key obstacle to accurate detection of arrhythmias, including AF, PVC and PAC. A method to separate clean ECG and pulse oximeter segments from segments with motion and noise artifacts in real time has been developed, thereby increasing the specificity of the identification of AF, PVC and PAC from NSR (see PCT Published Application WO 2012/051320, corresponding to WIPO (PCT) International Application Number PCT/US11/55989, filed on Oct. 12, 2011, entitled MOTION AND NOISE ARTIFACT DETECTION FOR ECG DATA, and PCT Publication No. WO 2012/051300, corresponding to PCT/US2011/055966, filed on Oct. 12, 2011, both of which are incorporated by reference herein in their entirety and for all purposes). Health monitoring using a smartphone is a nascent area, hence, there is scant literature on motion and noise artifact detection algorithms that are specific to mobile health monitoring. The Results section details various approaches that have been already implemented with the AF detection application to reduce motion and noise artifacts so that false positive detection of AF are minimized Detection of Bigeminy, Trigeminy and Quadrigeminy Patterns of PAC and PVC In one embodiment of these teachings, the determination of the bigeminy, trigeminy and quadrigeminy patterns of either PAC or PVC is based on the use of the Poincare plot. The Poincare plot is a well-recognized method for characterizing dynamic patterns that may occur in a time series by plotting the current data in relation to the system output at the past time point (see, for example, Sarkar S, Ritscher D, Mehra R. A detector for a chronic implantable atrial tachyarrhythmia monitor. IEEE Trans Biomed Eng. 2008; 55(3):1219-24, which is incorporated by reference herein is entirety and for all purposes). If the dynamics of the data are not random, nonlinear correlation present in the data will reveal certain phase structures in the Poincare plot. The present teachings enhance the conventional Poincare plot by forming several sectors to characterize various patterns of data, which include the AF and NSR, as well as bigeminy, trigeminy, quadrageminy and various combinations of these three patterns of PAC and PVC. A detailed explanation of this method and how it can be used to characterize various patterns of PAC and PVC is provided hereinbelow.

FIG. 1 shows a flowchart of one embodiment of the method of these teachings to detect AF, PVC and PAC from NSR, to discriminate among bigeminy, trigeminy, quadrigeminy and various combinations of these three patterns associated with both PAC and PVC, and to discriminate between PVC and PAC, all from smartphone data. (FIG. 1 can be expanded to include the use of Turning Point Ratio to differentiate between PAC and PVC.) The results, shown in Table 3, support that PVC and PAC can be successfully detected and discriminated in real time using the present teachings. In one instance, PVC and PAC can be successfully detected and discriminated in real time using the present teachings and using a smartphone as the measurement device.

Figure 2A:
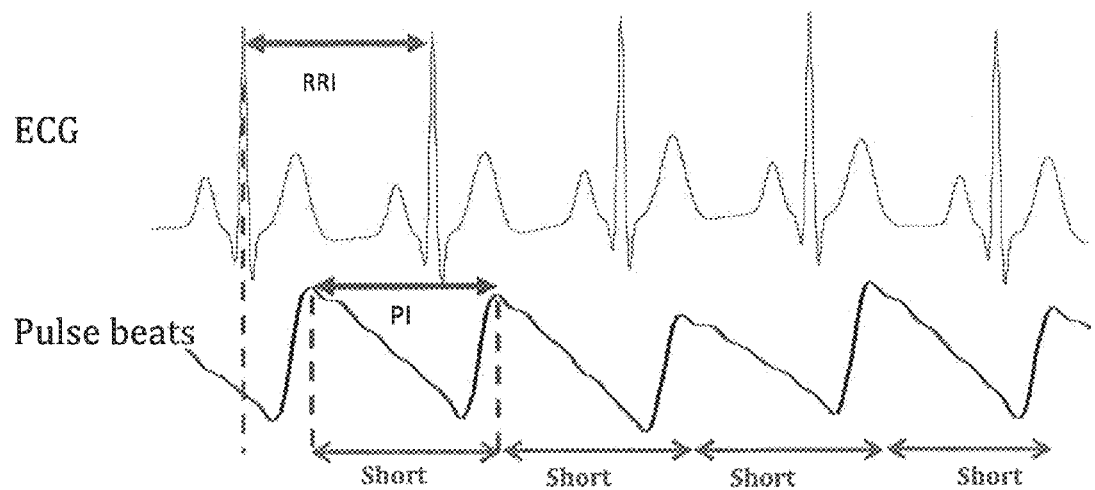
FIG. 2a is a Comparison of ECG RR intervals to pulse intervals obtained from an smartphone.
Figure 2B:
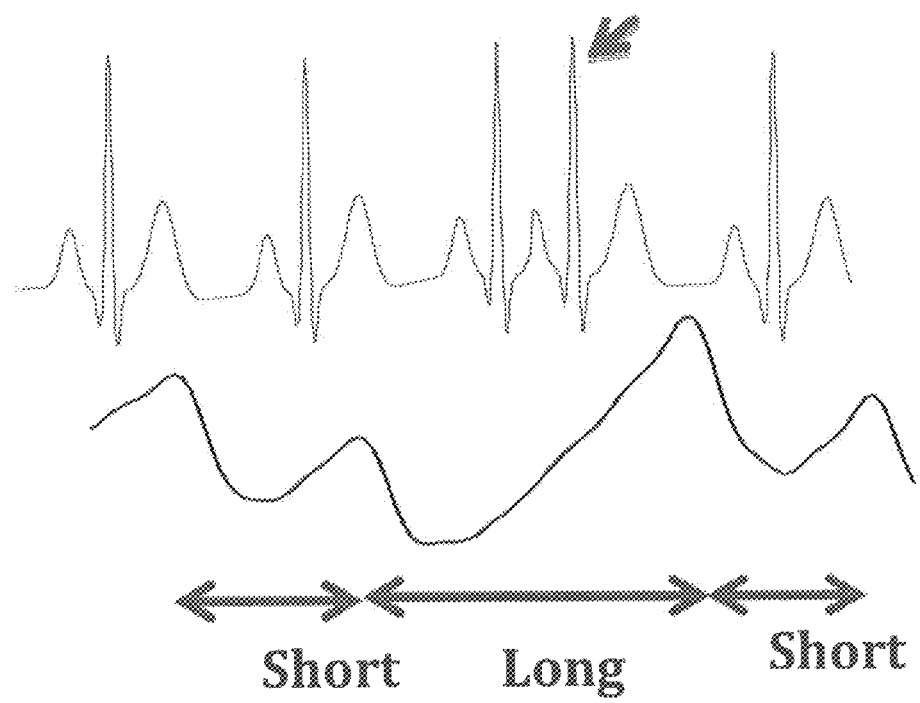
FIG. 2b is an example illustrating how a premature atrial contraction results in a longer duration pulse interval and larger amplitude pulse beat when compared to a normal pulse beat.
Figure 2C:
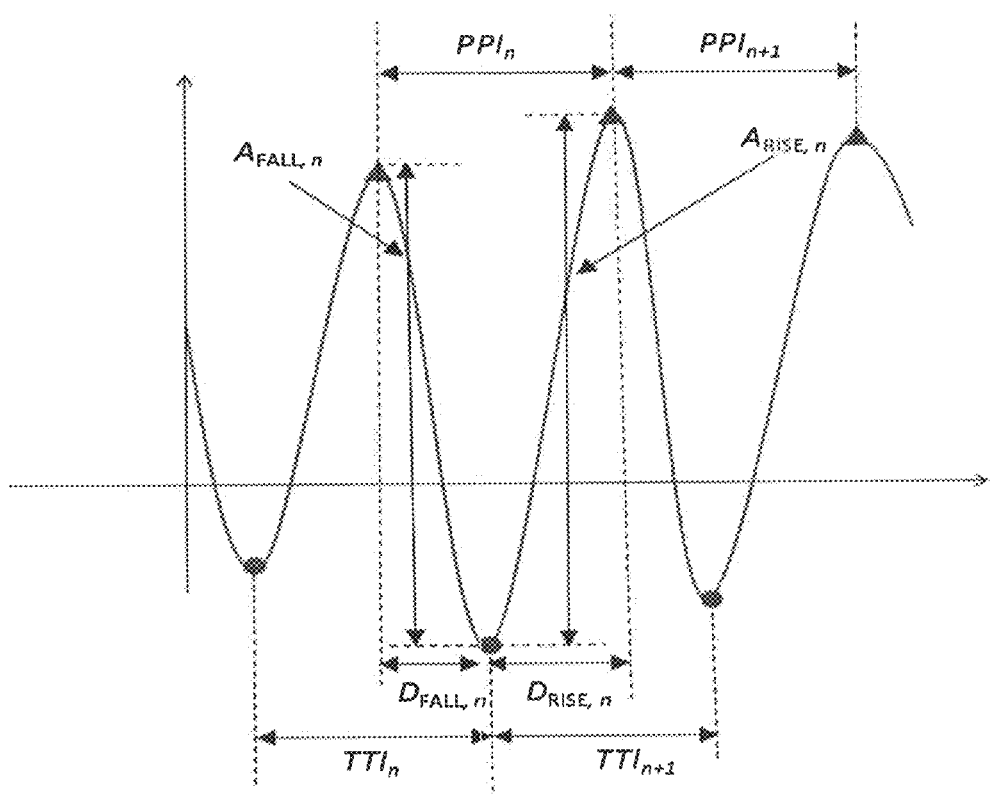
FIG. 2c shows a pulse intervals obtained from an smartphone and features extracted from the pulses.

In one embodiment, smartphone data can be used in the method of FIG. 1. In the present teachings, features can be extracted from the smartphone signal, e.g., peak-to-peak interval (PPI) and trough-to-trough interval (TTI), rise time ($D_{RISE}$) and fall time ($D_{FALL}$) from the measured pulsatile time series. As shown in FIG. 2c, the PPI is calculated by the difference between two successive peak times, $T_{PEAK,n} - T_{PEAK,n-1}$, and TTI is obtained by the difference between two successive trough times, $T_{TROUGH,n} - T_{TROUGH,n-1}$. $D_{RISE}$ is defined by the difference between the peak and the trough of the $n^{th}$ pulse, $T_{PEAK,n} - T_{TROUGH,n}$, while $D_{FALL}$ is the difference between the trough of the $n^{th}$ pulse and the peak of the n-1$^{th}$ pulse and, $T_{TROUGH,n} - T_{PEAK,n-1}$. Similarly, $A_{RISE}$ is $Y_{PEAK,n} - Y_{TROUGH,n}$ while $A_{FALL}$ is $Y_{PEAK,n-1} - Y_{TROUGH,n}$. PPI and TTI are used to discriminate between AF, PAC/PVC and NSR as well as identify specific patterns (bigeminy, trigeminy, and quadrigeminy) of PAC/PVC.

The first portion of the method shown in FIG. 1 compares the RMSSD, SE and TPR of PPI to their corresponding thresholds, respectively. If both of them are less than their thresholds, the pulsatile time series is classified as NSR without PAC or PVC (see the first condition in the flowchart in FIG. 1). Otherwise, the algorithms goes to next step and checks if the pulsatile time series is AF or PAC/PVC.

Figure 3:
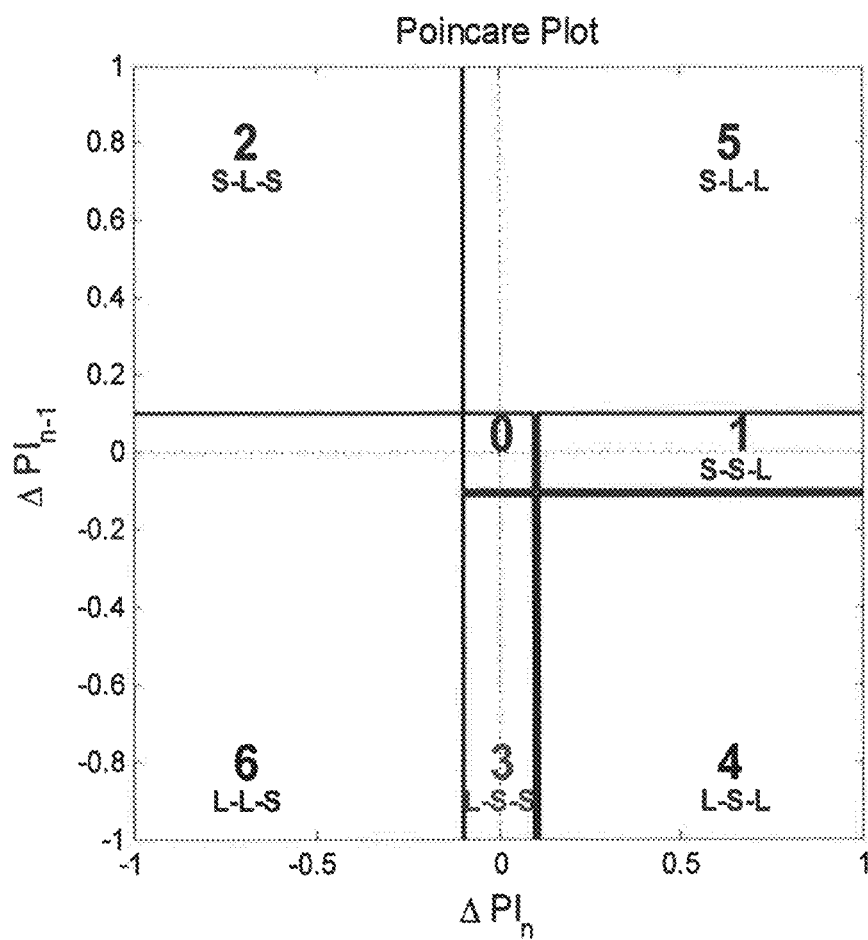
FIG. 3 is Poincare plot divided into six regions. AF, NSR, PVC and PAC rhythms will have different trajectory patterns and they may be confined to only a single region or multiple regions as demonstrated in FIG. 4.

Poincare Plot to differentiate bigeminy, trigeminy and quadrigeminy patterns of PAC and PVC: A Poincare plot is used to quantify the self-similarity in time series $x_i$, by drawing a two-dimensional plot with $(x_{i-1}, x_i)$ for i=2, 3, . . . , N. Poincare plots have been applied for AF detection with RR interval time-series derived from an ECG signal with good results (15). For one embodiment, pulse data signals from a smartphone are used instead of ECG signals. Note that a pulse interval from a smartphone recording (bottom panel) is similar to an RR interval derived from an ECG signal (top panel) as shown in FIG. 2a. Shown at the bottom panel of FIG. 2b is a PAC episode obtained from a subject using an iPhone recording and the top panel represents the corresponding ECG data. A frequency of occurrence of PAC and PVC at every 2nd, 3rd and 4th pulse beats are known as bigeminy, trigeminy and quadrigeminy, respectively. When a PAC episode occurs as noted by an extra, premature ECG beat on the top panel of FIG. 2b (noted by an arrow) the corresponding pulse beat at the rising phase of the waveform in the bottom panel of FIG. 3b is markedly prolonged. Hence if the difference between the consecutive normal pulse beat and the PAC pulse beat (ΔPI) is obtained, a "long" pulse interval will be obtained as compared to two consecutive normal pulse beats, which is termed the "short" pulse interval. To facilitate complete discrimination among bigeminy, trigeminy and quadrigeminy patterns of the PAC and PVC, the Poincare plot will be divided into six regions as shown in FIG. 4. The six regions represent permutations of all possible sequences of "long" and "short" based on 3 consecutive pulse intervals which are derived from 4 consecutive beats as detailed in Table 1. The boundaries demarcating each of the six regions in FIG. 3 were derived from 95 subjects' smartphone recordings (88 subjects from pre- and post-cardioversion and 4 subjects with PAC and 3 subjects with PVC).

TABLE 1

Poincare plot sectors corresponding to PAC/PVC patterns which consist of bigeminy, trigeminy and quadrigeminy.

| $PI_{i-2}$-$PI_{i-1}$-$PI_i$ | Region $ID_i$ |
|---|---|
| Short-Short-Long | 1 |
| Short-Long-Short | 2 |
| Long-Short-Short | 3 |
| Short-Short-Short | 0 |
| Long-Long-Long | 0 |
| Long-Short-Long | 4 |
| Short-Long-Long | 5 |
| Long-Long-Short | 6 |

Figure 4A:
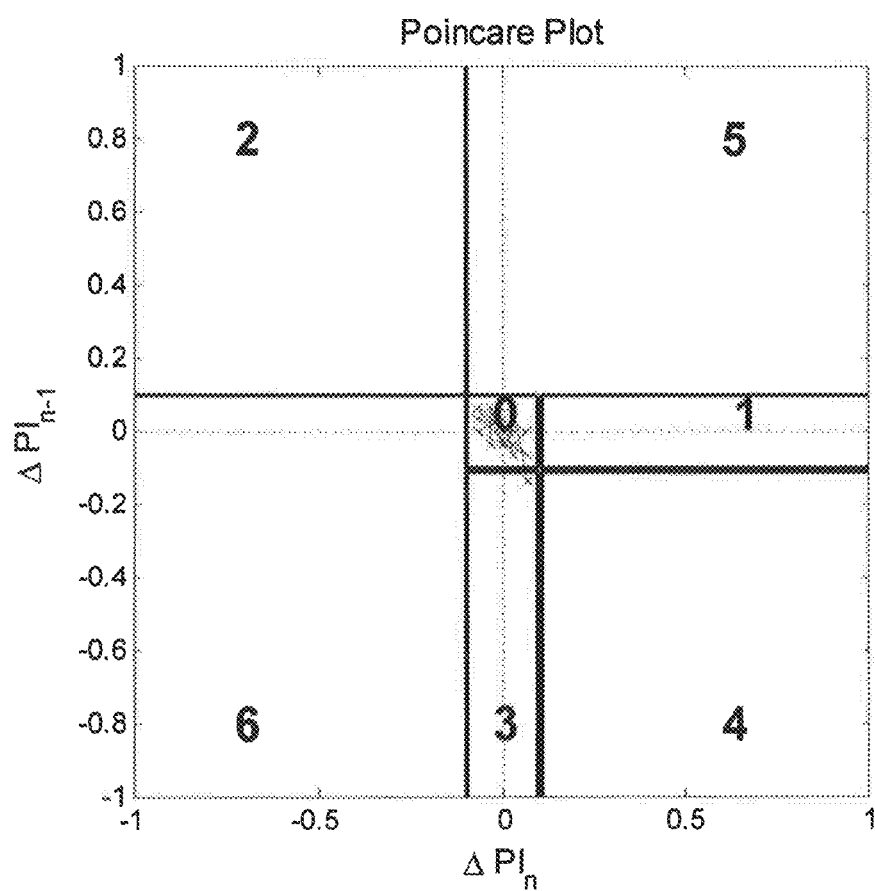
FIGS. 4a-4d are Poincare plots with ($\Delta PI_{i-1}$, $\Delta PI_i$) trajectory. (a): NSR: (b): AF, (c): PVC-quadrigeminy, (d): PVC-trigeminy.
Figure 4B:
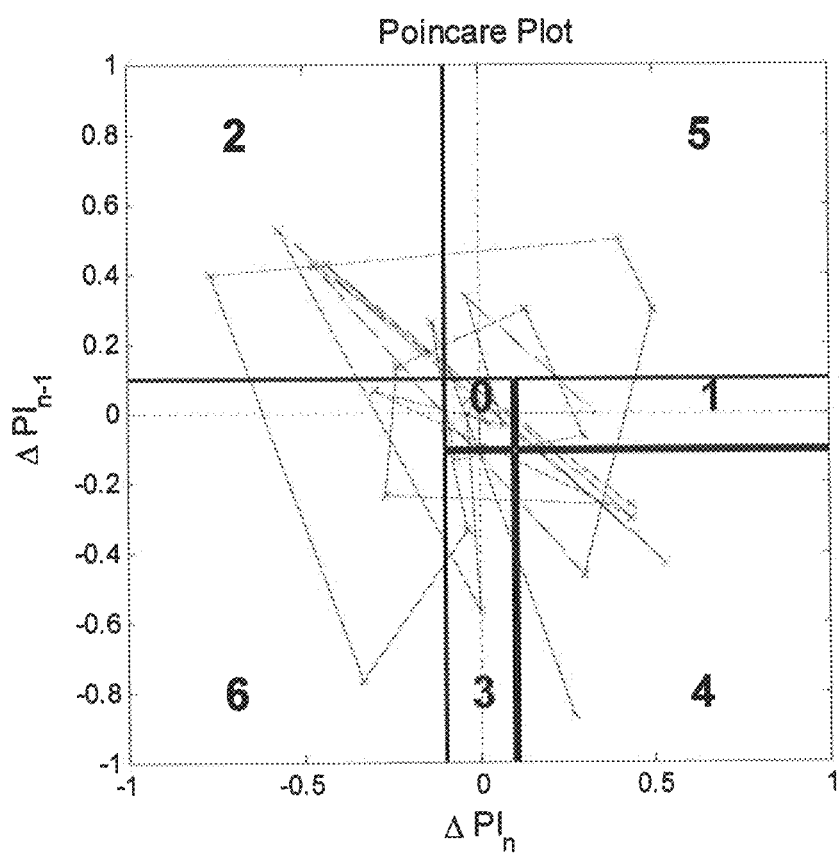
Figure 4C:
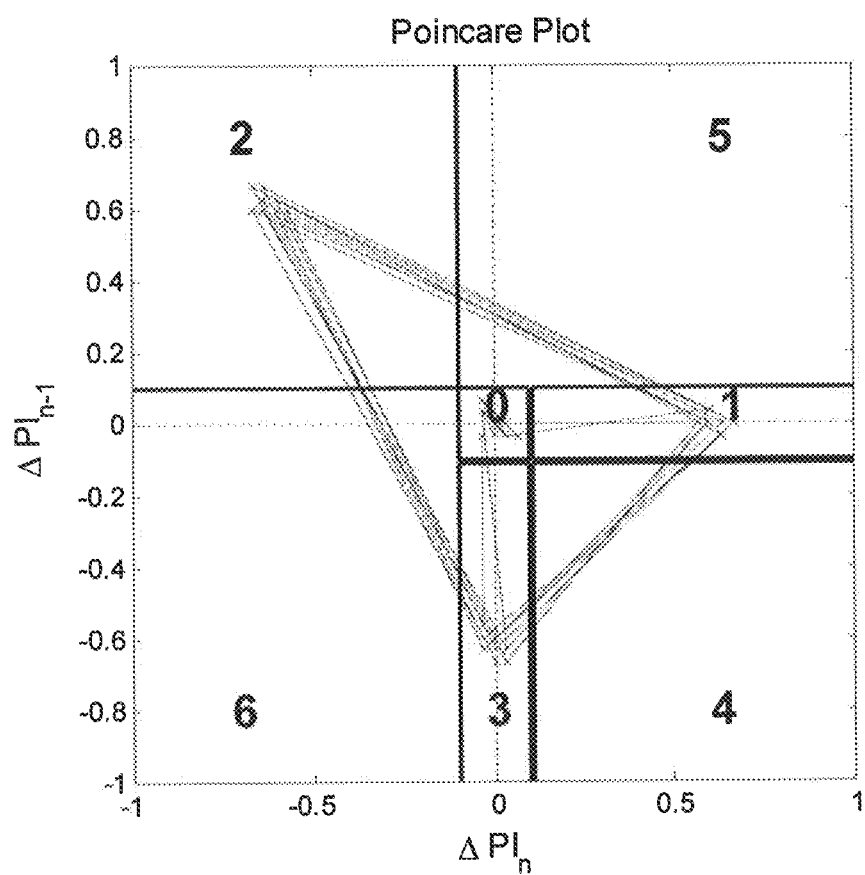
Figure 4D:
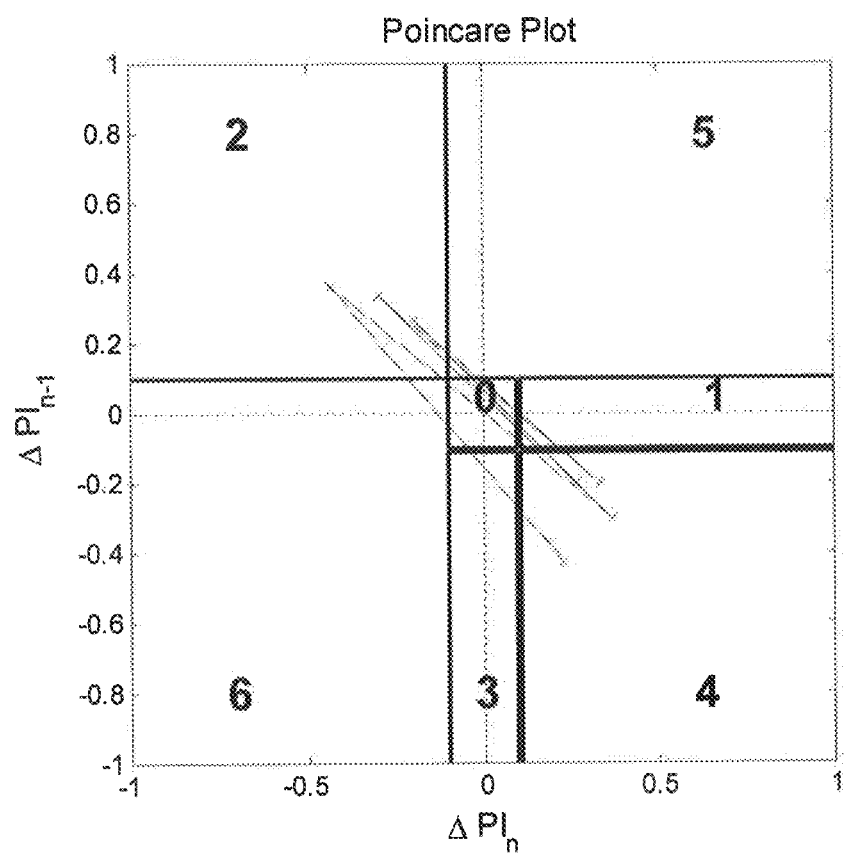
Figure 5A:
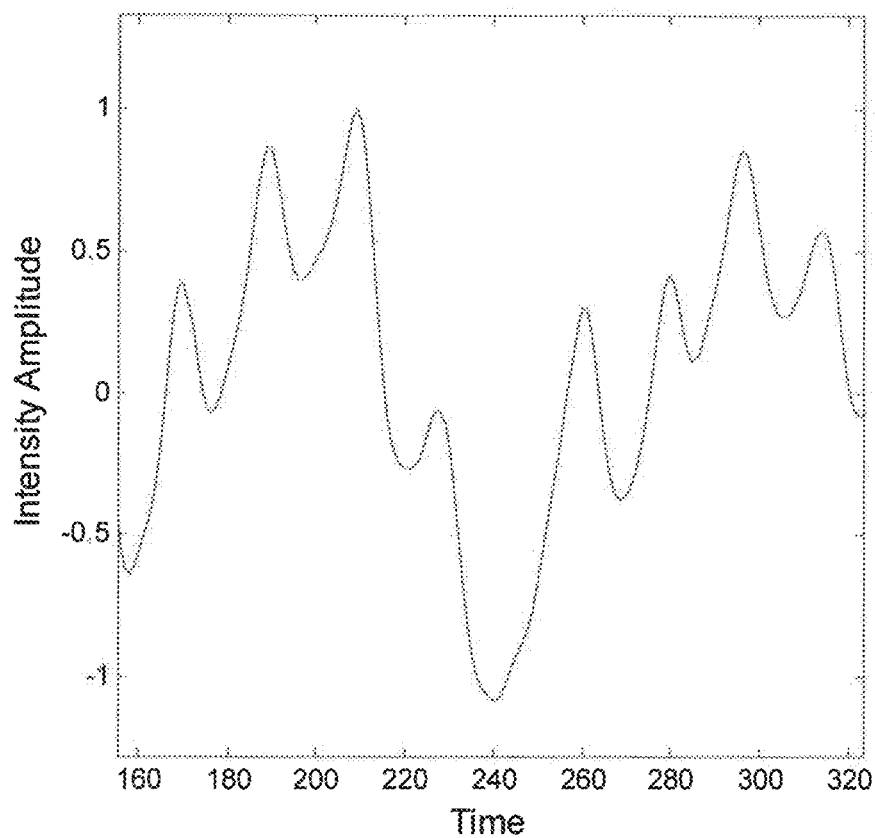
FIG. 5a-5d show representative smartphone data for (a): PVC, (b): PVC's peak amplitude histogram for KL divergence, (c): PAC and (d): PAC's peak amplitude histogram for KL divergence.
Figure 5B:
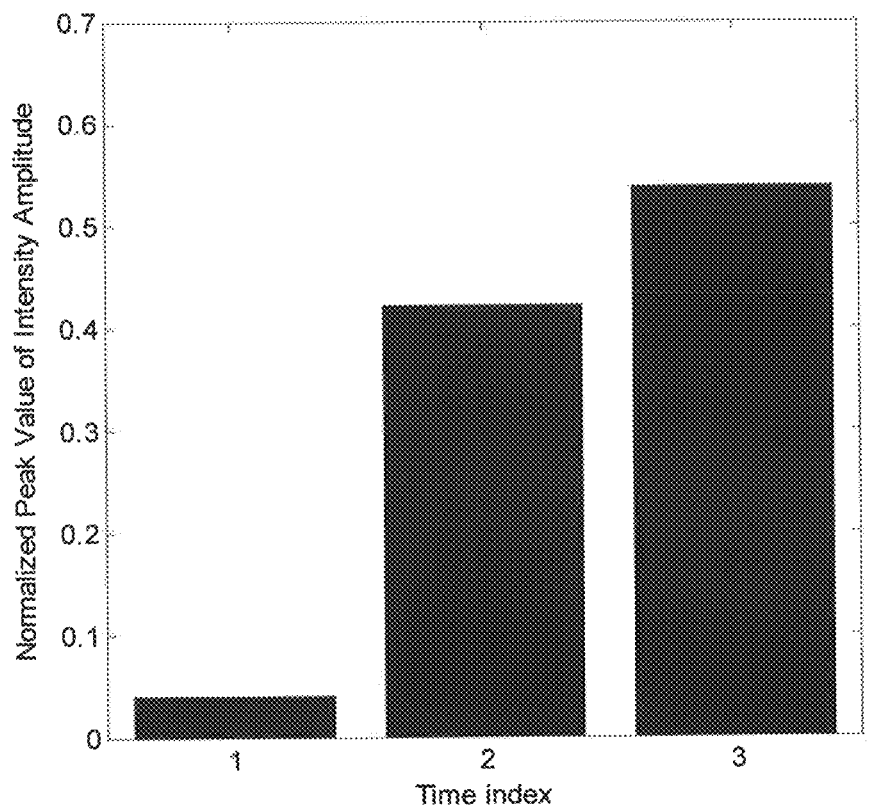
Figure 5C:
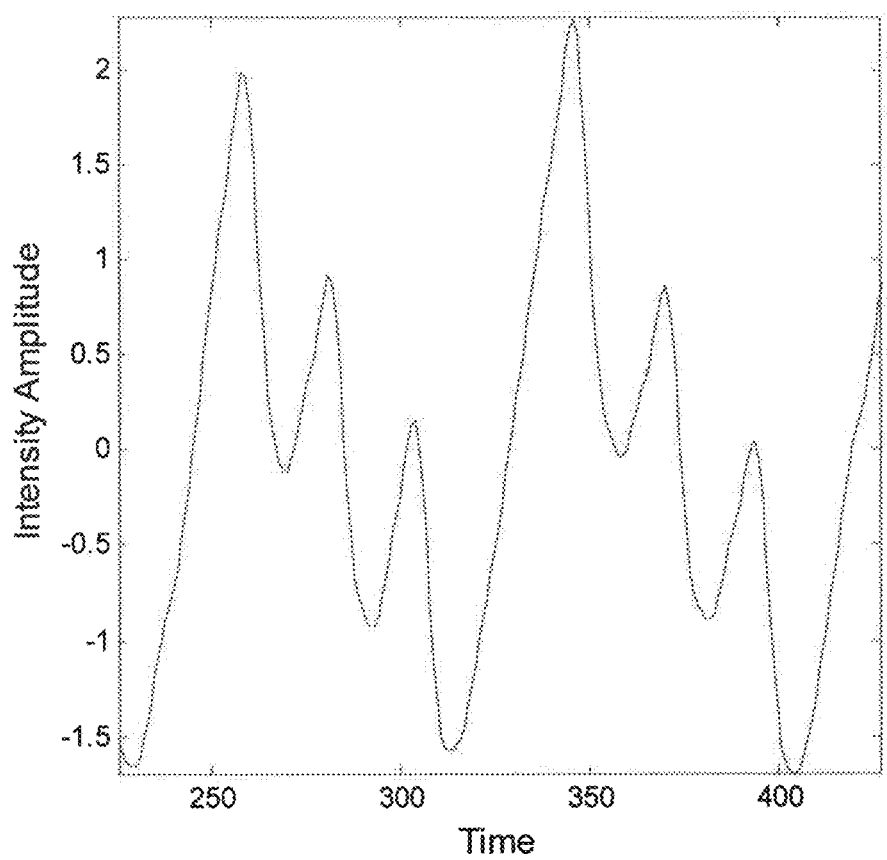
Figure 5D:
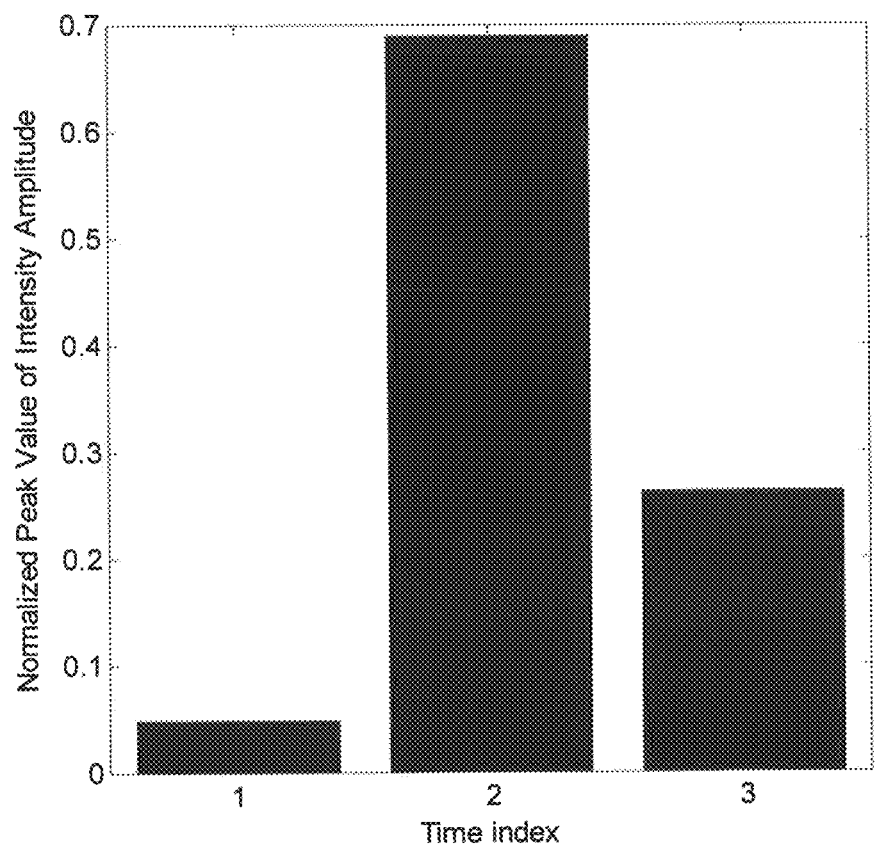

The Poincare patterns of ΔPI trajectories shown in Table 2 are based on 2 minute smartphone data from each of the 88 NSR subjects (post-cardioversion), 88 AF subjects (pre-cardioversion), 3 PVC subjects, and 4 PAC subjects. The Poincare pattern for NSR is largely confined within the region "0" as shown in FIG. 4a. Hence, in Table 2, the trajectory pattern is labeled as "0-0-0-0-0-0- . . . for the entire 2 minutes of data for 88 NSR subjects. As expected for AF, the Poincare patterns are random and the trajectories cross all six regions as shown in FIG. 4b. For both PVC and PAC's quadrigeminy, the Poincare plot shows repeating triangle patterns spanning the regions 1, 2 and 3, as shown in FIG. 5c. Similarly, the trigeminy of the PVC and PAC show repeating patterns spanning the regions 2 and 4 as shown in FIG. 4d. Finally, the bigeminy of the PVC and PAC will be similar to NSR patterns, spanning only the region "0". However, bigeminy can be discriminated from NSR by noting that its time duration is longer and the amplitude of the rising phase of the pulse amplitude is larger than in NSR.

TABLE 2

Arrhythmia with its corresponding ($\Delta PI_{i-1}$, $\Delta PI_i$) trajectory pattern in Poincare plot

| Type of Arrhythmia | Trajectory Patterns in the Poincare plot's six regions ($\Delta PI_{i-1}$, $\Delta PI_i$) |
|---|---|
| Premature Atrial Contraction (PAC) | |
| Bigeminy | 0-0-0-0-0-0- . . . |
| Trigeminy | 2-4-2-4-2-4- . . . |
| Quadrigeminy | 1-2-3-1-2-3- . . . |

TABLE 2-continued

Arrhythmia with its corresponding ($\Delta PI_{i-1}, \Delta PI_i$) trajectory pattern in Poincare plot

| Type of Arrhythmia | Trajectory Patterns in the Poincare plot's six regions ($\Delta PI_{i-1}, \Delta PI_i$) |
|---|---|
| Premature Ventricular Contraction (PVC) | |
| Bigeminy | 0-0-0-0-0-0- ... |
| Trigeminy | 2-4-2-4-2-4- ... |
| Quadrigeminy | 1-2-3-1-2-3- ... |
| Normal Sinus Rhythm (NSR) | 0-0-0-0-0-0- ... |
| Atrial Fibrillation (AF) | irregular patterns with trajectories at all 6 possible regions |

The Poincare plot is used to look for the trajectory patterns as detailed in Tables 2-3 to discriminate between bigeminy, trigeminy, and quadrageminy patterns associated with the PAC or PVC. Note that various combinations of these three patterns associated with the PAC or PVC will also be distinct from either the NSR or AF. For example, the trajectory patterns associated with various combinations of bigeminy, trigeminy or quadrigeminy will not be confined in the region "0" (e.g. for NSR) and the trajectory magnitudes will be much larger than for the NSR. In addition, these combinations of PAC and PVC patterns will have more orderly patterns (since the phase trajectory patterns will largely be confined to regions 0, 1, 2, 3 and 4 as shown above) than the random trajectory patterns associated with AF (trajectory patterns are evident in all regions of the Poincare plot). Hence, various combinations of bigeminy, trigeminy or quadrigeminy will also be distinguishable from both NSR and AF.

B: Use of Kullback-Leibler (KL) Divergence Algorithm to Differentiate Between PAC and PVC:

The KL divergence algorithm is a measure of the difference between two probability distributions p(x) and q(x), as defined by:

$$KL(p\|q) = -\int p(x) \log\left\{\frac{q(x)}{p(x)}\right\} dx.$$

Figure 6:
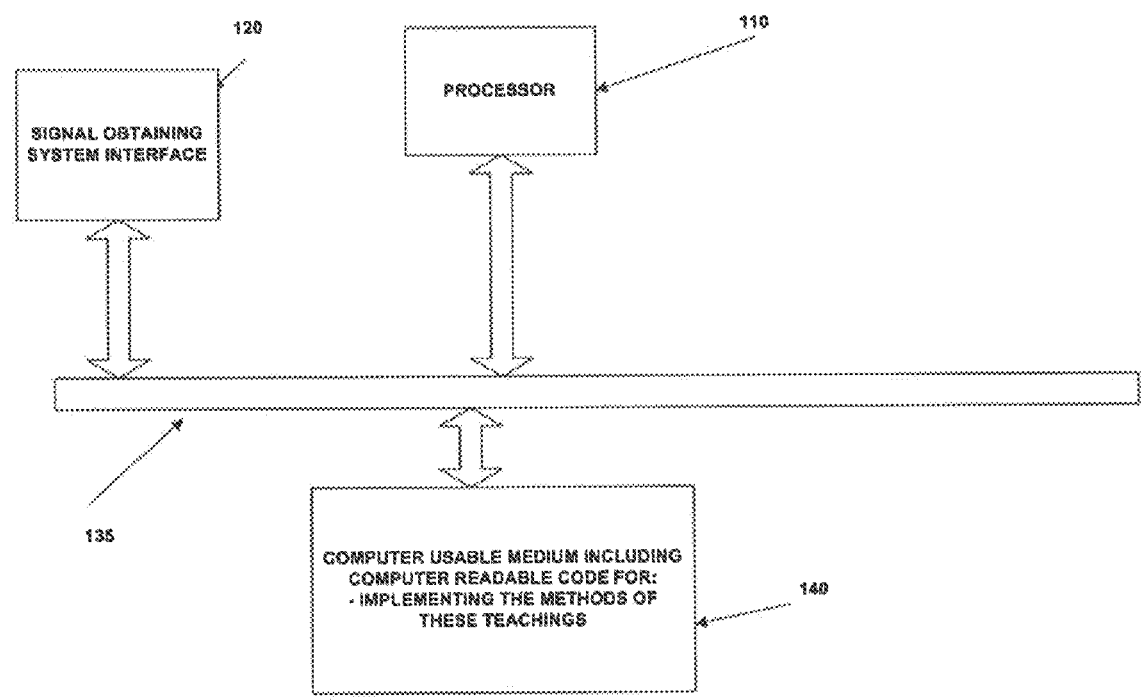
FIG. 6 shows one embodiment of the system of these teachings.

The p(x) is the known probability distribution representing either PAC or PVC, and q(x) is the probability distribution of the measured data. Since the divergence of the two probability distributions, p(x) and (x) is being examined, we look for the minimum value of KL(p∥q). The preliminary results from 3 subjects with PVC and 4 subjects with PAC are used to illustrate discrimination between these two arrhythmias using the KL divergence algorithm. Representative PVC and PAC recordings are shown in FIG. 6. From each of these two data sets, histograms (probability distributions) of their peak amplitude values, as shown in FIG. 6, are determined. Note the clear difference in the histograms between PVC and PAC. These two histograms are denoted as p1(x) and p2(x) for the PVC and PAC, respectively. With larger clinical databases containing PAC and PVC, their histograms will better represent the population sample characteristics. Hence, a new data set's histogram or its probability distribution, q(x), will be compared to the population database probability distributions p1(x) and p2(x) to examine if there is a match with either of the two distributions to that of q(x).

C: Use of Turning Point Ratio to Differentiate Between PAC and PVC:

In addition, another approach to discriminate trigeminy and quadrigeminy patterns of PAC and PVC using a method called Turning Point Ratio (TPR) is described. To detect a quadrigeminy, "Short-Short-Long-Short-Short (SSLSS)" repeating pulse interval patterns are searched for. In one embodiment, using the stochastic theory, it has been found that the expected number and standard deviation of detecting PAC and/or PVC quadrigeminy can be detected by using the following mean and standard deviation value of the pulse intervals:

$$\mu_{TP} = \frac{l-4}{5},$$

$$\sigma_{TP} = \sqrt{\frac{5l-27}{50}},..$$

In the example of SSLSS of l=45, the mean of turning point ($\mu TP$)=8.2 and the standard deviation $\sigma TP$=1.99. A PPG segment is considered random if the number of turning points (or TPR) falls within some threshold confidence interval (TprThresh) of the expected TPR. Otherwise, a PPG segment is considered to exhibit quadrageminy patterns.

For trigeminy, the TP is defined as the pulse intervals exhibiting "Short-Long-Short (SLS)" or "Long-Short-Long (LSL)" patterns.

The expected number and standard deviation of detecting PAC trigeminy TPs in a segment l are given by $$\mu_{TP} = \frac{2l-4}{3},$$

$$\sigma_{TP} = \sqrt{\frac{16l-29}{90}},$$

A PPG segment is considered random if the number of turning points (or TPR) falls within some threshold confidence interval (TprThresh) of the expected TPR. Otherwise, a PPG segment is considered to exhibit trigeminy patterns.

In another embodiment, to apply TPR in discriminating PAC/PVCs, a TP is redefined as a point where a specific pattern starts, e.g. bigeminy, trigeminy and quadrigeminy patterns. If an unknown time series has similar number of TP (or TPR), related to a specific pattern, to that of an independent time series, the unknown series is expected to be independent. Otherwise, the time series is expected to be dependent. To detect a quadrigeminy, $TP_{QUAD}$ is defined as a starting point of "Short-Short-Long-Short-Short-Long-Short-Short (SSLSSLSS)" in a PPI sequence. Considering an independent time sequence $x_i$, the probability of a point being quadrigeminy TP is given by:

$$PR\{X_{i-2} < X_i, X_{i-1} < X_i, X_i > X_{i+1}, X_i > X_{i+2},$$

$$X_{i+3} > X_{i+1}, X_{i+3} > X_{i+2}, X_{i+3} > X_{i+4}, X_{i+3} > X_{i+5}\} =$$

$$\int_{x=-\infty}^{\infty} Pr\{x > X_{i-1}\} Pr\{x > X_{i-2}\} Pr\{x > X_{i+1}, x > X_{i+2}, X_{i+1} < X_{i+3},$$

$$X_{i+2} < X_{i+3}, X_{i+4} < X_{i+3}, X_{i+5} < X_{i+3}\} f(x) dx =$$

$$\int_{x=-\infty}^{\infty} \left\{\frac{1}{3} F(x)^4 - \frac{F(x)^7}{30}\right\} f(x) dx = \frac{1}{16}$$

Using the stochastic theory, the expectation $\mu_{TP,quad}$ and standard deviation $\sigma_{TP,quad}$ of the number of quadrigeminy TPs in a segment l are given by $$\mu_{TP,QUAD} = \frac{l-7}{16}, \sigma_{TP,QUAD} \approx \sqrt{0.0601l - 0.4255}$$

For example, an independent pulsatile time series with l=45 has $\mu_{TP,QUAD}$ and $\sigma_{TP,QUAD}$ of 1.435 and 1.1737, respectively. A PPG segment is considered independent if the number of TPs (or TPR) falls within some threshold confidence interval TpThresh (or TprThresh) of the expected TP (or TPR). Otherwise, a PPG segment is not considered to be dependent.

For trigeminy, the $TP_{TRI}$ are defined as a starting point where "Short-Long-Short-Long-Short (SLSLS)" PPI pattern begins. Hence, the probability of being $TP_{TRI}$ is similarly given by:

$$Pr\{X_{i-1} < X_i > X_{i+1} < X_{i+2} > X_{i+3}\} =$$
$$\int_{-\infty}^{\infty} Pr\{X_{i-1} < x\} Pr\{x > X_{i+1} < X_{i+2} > X_{i+3}\} f(x) dx =$$
$$\int_{-\infty}^{\infty} \left( \frac{F(x)^2}{2} - \frac{F(x)^4}{6} \right) f(x) dx = \frac{2}{15}$$

The $\mu_{TP,TRI}$ and $\sigma_{TP,TRI}$ are given by:

$$\mu_{TP,TRI} = \frac{2(\ell - 4)}{15}, \sigma_{TP,TRI} \approx \sqrt{0.0826\ell - 0.2527}$$

For bigeminy, TPs are defined as a starting point where "Long-Long (LL)" PPI pattern starts. PAC/PVC bigeminy is appropriately discriminated by the mean and variance than TPR since the TPR of PAC/PVC is expected to be similar to that of NSR.

In one or more embodiments, the method of these teachings for discriminating between atrial fibrillation and premature ventricular contractions (PVC) and premature atrial contractions (PACs) includes demarcating boundaries in a Poincare plot space, the boundaries being obtained from data from a test set of test subjects, the Poincare plot space being a space of time interval between consecutive pulses obtained by sensing variability in heart rate signal, constructing a Poincare plot of time interval data from a subject under test, the time interval being a time interval between consecutive pulses obtained by sensing variability in heart rate signal from the subject under test, identifying data in patterns in the Poincare plot, obtaining updated data by subtracting the data in the patterns from the time interval data from the subject under test, obtaining a root mean squared of successive differences, a Shannon entropy and a turning point ratio for the updated data, comparing the root mean square of successive differences to a first predetermined threshold; comparing the Shannon entropy to a second predetermined threshold, comparing the turning point ratio to a third predetermined threshold, determining, if each of the root mean square of successive differences, the Shannon entropy, and the turning point ratio is less than a corresponding predetermined threshold, the subject under test has atrial fibrillation and determining, if at least one of the root mean square of successive differences, the Shannon entropy, and the turning point ratio is at least equal to a corresponding predetermined threshold, the subject under test has normal sinus rhythm (NSR) with PVC or PAC.

In one instance, the method of these teachings also includes constructing a first probability distribution for peak amplitude data from the subject under test, obtaining a first Kullback-Leibler divergence for a second probability distribution and the first probability distribution; the second probability distribution being constructed from peak amplitude data for another test set of subjects with PAC, obtaining a second Kullback-Leibler divergence for a third probability distribution and the first probability distribution; the third probability distribution being constructed from peak amplitude data for yet another test set of subjects with PVC, determining that the subject under test has NSR with PAC if the first Kullback-Leibler divergence is greater than the second Kullback-Leibler divergence, and determining that the subject under test has NSR with PVC if the first Kullback-Leibler divergence is at most equal to the second Kullback-Leibler divergence.

In another instance, the method of these teachings also includes determining whether a PAC or PVC pattern is quadrigeminy pattern by: identifying whether repeating pulse interval patterns are "short-short-long-short-short" (SSLSS) patterns, determining a number of turning points in identified SSLSS patterns, determining an expected number of turning points by a predetermined relation, comparing a difference between the number of turning points and the expected number of turning points to a fourth predetermined threshold and determining, if the difference is greater than the fourth predetermined threshold, that the PAC or PVC pattern is a quadrigeminy pattern.

In yet another instance, the method of these teachings also includes determining whether a PAC or PVC pattern is trigeminy pattern by identifying whether repeating pulse interval patterns are "short-long short" (SLS) or "long-short-long" (LSL) patterns, determining a number of turning points in identified patterns, determining an expected number of turning points by a predetermined relation, comparing a difference between the number of turning points and the expected number of turning points to a fourth predetermined threshold and determining, if the difference is greater than the fourth predetermined threshold, that the PAC or PVC pattern is a trigeminy pattern.

In another embodiment, the method of these teachings also includes obtaining, before demarcating boundaries in the Poincare plot space, a second root mean square of successive differences, a second Shannon entropy and a second turning point ratio for the time interval data from a subject under test, comparing the second root mean square of successive differences to a fourth predetermined threshold; comparing the second Shannon entropy to a fifth predetermined threshold, comparing the second turning point ratio to a sixth predetermined threshold, determining, if each of the second root mean square of successive differences, the second Shannon entropy, and the second turning point ratio is less than a corresponding predetermined threshold, that the subject under test exhibits NSR without PAC or PVC and ending, if the subject under test exhibits NSR without PAC or PVC, the method.

Figure 7:
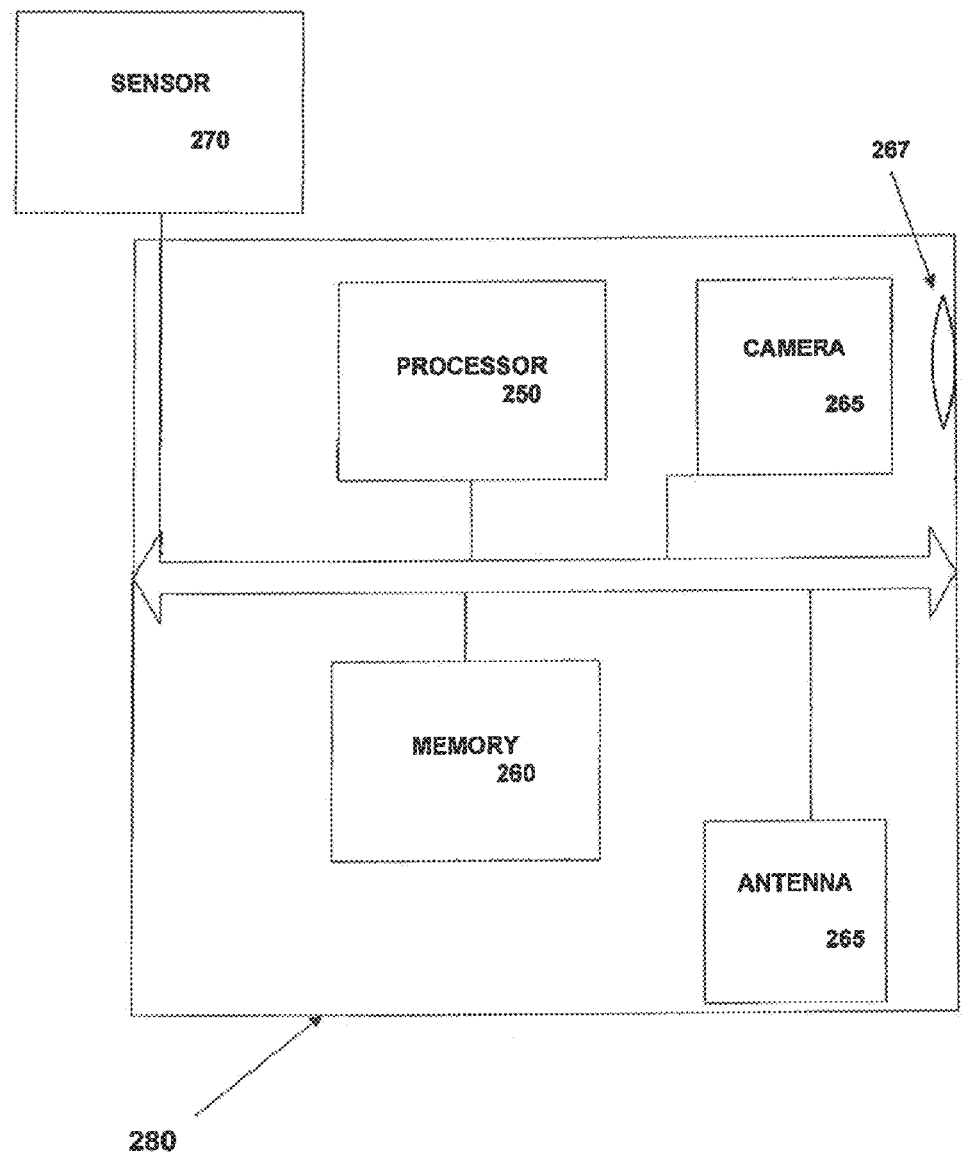
FIG. 7 shows another embodiment of the system of these teachings.
Figure 8:
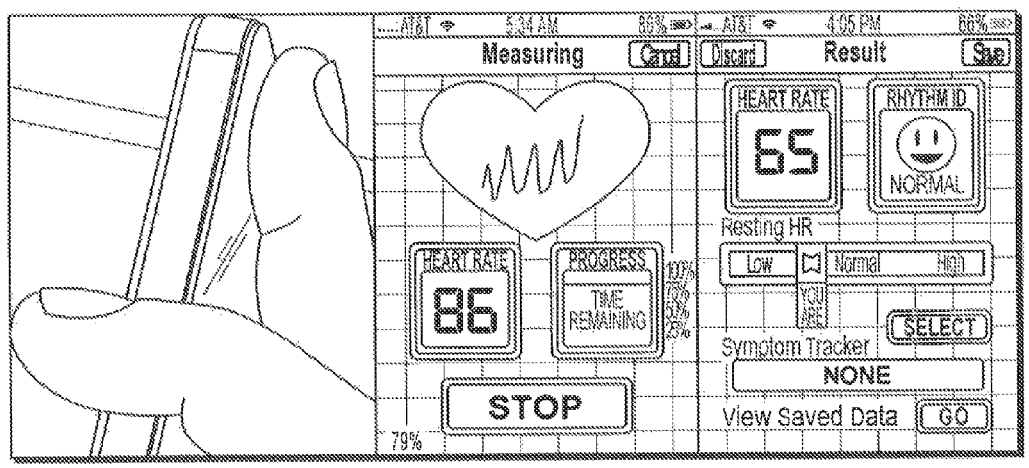
FIG. 8 represents a smart phone application for data recording (the application uses the camera lens and illumination to acquire information about heart rate and rhythm).

In another embodiment, in the method of these teachings, the heart rate signal from the subject under test is obtained using a handheld mobile communication device, such as, but not limited to, that shown in FIGS. 7 and 8. In one instance, sensing variability in heart rate signal from the subject under test includes detecting signal from triaxial accelerometers in the handheld mobile communication device, obtaining a kurtosis value for a signal from each triaxial accelerometer, comparing the kurtosis value for the signal for each triaxial accelerometer to a predetermined threshold, and acquiring the heart rate signal from the subject under test, only if the kurtosis value for each accelerometer is at most equal to the predetermined threshold.

FIG. 6 shows a block diagram of an embodiment of the system of these teachings. Referring to FIG. 6, in the embodiment shown there in, the system includes an interface 120 to a signal obtaining subsystem, the signal obtaining subsystem providing the signal related to R-R intervals, one or more processors 110 and computer readable media 140 having a computer readable code, the computer readable code causing the processor to implement the method of these teachings. The interface 120, the one or more processors 110 and the computer readable media 140 are operatively connected by a connection component 135 (such as, but not limited to, a computer bus).

Currently, clinical AF monitoring is primarily performed if a patient describes symptoms that a clinician interprets as possibly being secondary to a cardiac arrhythmia. Given that paroxysmal and asymptomatic AF is a growing clinical and public health problem, better, cheaper, and more readily available AF detection technology is needed. Given the ever-growing popularity of smart phones, our approach to AF detection using a smart phone will give the population as well as health care providers the opportunity to monitor AF under a wide variety of conditions outside of the physician's office and even outside of the home. Because our approach does not involve a separate ECG sensor but instead uses only standard smart phone hardware, it is cost-effective, thereby leading to better acceptance and use by patients. Our mobile health (mHealth) for AF detection platform has the potential to markedly change the traditional delivery of AF healthcare, allowing for more frequent, rapid, and personally-initiated AF detection. Ownership of mobile phones has increased markedly among older individuals, a subgroup at particularly high risk for AF, as illustrated by the fact that 80% of Americans older than 65 currently use mobile phones. Since the proportion of new smart phones sold is increasing at the fastest rate in the mobile phone category, the penetration of hardware necessary to use our AF detection application is rapidly growing. With respect to the potential acceptability of our AF detection platform among at-risk individuals, it is notable that survey data suggest that patients prefer to use mHealth for their healthcare than traditional diagnostic methods. Recent survey data suggest that mobile phones are the device of choice among people over 50 for mHealth applications. Moreover, a large percentage of surveyed individuals expressed a desire to use their mobile phones (including smart phones as their penetration is expected to surge from 23.0% in 2009 to 67.1% by 2015) for health management even if such technology was not currently available (27). Our group is uniquely positioned to leverage existing smart phone technologies to detect AF since the clinical use of a real-time, automated AF-detection algorithm has been previously developed and validated; most recently involving 76 persistent AF subjects pre- and post-cardioversion at UMass Medical Center. Moreover, a major medical device corporation (ScottCare Corporation) has licensed our AF algorithm and a commercially available, real-time AF monitoring device currently incorporates it. ScottCare is interested in additional technology transfer agreements with us related to AF with motion and noise artifact detection algorithms on the promise of the successful outcome of the work proposed. Further, these teachings can significantly improve the accuracy of the AF algorithm as our preliminary results indicate that discriminating PVC and PAC from AF episodes should be successful. One impact of these teachings is that these teachings will result in rapid translation into innovative AF, PVC and PAC detection technology (in both conventional monitors and smartphone apps if commercialized), leading to more effective monitoring and accurate diagnosis of AF.

Physiological parameter monitoring from a smart phone. The previously developed application developed for heart rhythm data collection using an iPhone 4s (a version of which has also been prototyped for HTC, Motorola and Samsung smart phones) is shown in FIG. 8. Details regarding data collection and pre-processing of data are provided hereinabove. A section of an example GREEN signal (camera recording has Red, Green and Blue wavelengths) sampled at ~30 frames per second obtained during spontaneous breathing is shown in FIG. 8. The pulse signal is similar to a standard pulse-oximeter signal. Peak detection was performed to identify the HR signal along with that obtained from a simultaneous ECG after R-wave peak detection. The mean heart rate±SD was 92.2±5.3 for HRECG and 92.3±5.9 for HRGREEN on 52 subjects indicating that accurate peak detection can be obtained even with the low sampling rate of a smartphone. A peak detection algorithm was developed in the present teachings because the standard ECG peak detection algorithms do not work, as they are based on sampling rates greater than 200 Hz. The algorithm for pulse beat detection consists of interpolation, sudden DC change elimination, two stages of band pass filter, derivative rank filter and matching of original peaks. The interpolation is to make the time increment constant since the actual image frame rate varies depending on the internal processing load of the smart phone; the average frame rate of an iPhone 4s is 29.50 fps with a standard deviation of 4.62 fps. The pulsatile signal was interpolated to 30 Hz using a cubic spline algorithm. The sudden DC change elimination is necessary because of the camera's exposure to inadvertent external light sources, which can be due to incorrect finger positioning or finger movement during recording. Two stages of band pass filter were used to calculate instantaneous heart rate. The derivatives rank filter was used to find the dominant peak within each heart rate pulse, and the matching original peaks were used to convert the peak time from the derivatives signal to the original pulsatile signal. The capability to extract accurate HR signals, heart rate variability dynamics, the respiratory rates and oxygen saturation information directly from the green, red, and blue band signals from a smart phone is detailed in our recently published paper (see also PCT Publication No. WO2012100175, corresponding to PCT/US2012/022049, PHYSIOLOGICAL PARAMETER MONITORING WITH A MOBILE COMMUNICATION DEVICE, filed on Jan. 20, 2012, and corresponding U.S. Published application 2012190947, PHYSIOLOGICAL PARAMETER MONITORING WITH A MOBILE COMMUNICATION DEVICE, which are incorporated by reference herein in their entirety and for all purposes).

iPhone 4s for AF detection in 76 participants with AF: Pulsatile time series data were collected on 76 subjects with known persistent AF who underwent successful electrical cardioversion to normal sinus rhythm using a prototype iPhone 4S application. Participants underwent rhythm assessment using a novel iPhone 4S application before (AF) and after (no AF) electrical cardioversion. The camera of an iPhone 4s was placed on either the index or middle finger of study participants for 2 minutes prior to, and immediately after, cardioversion. Data were recorded with patients in the supine position with spontaneous breathing. Standard 12-lead ECG or telemetry tracings were obtained concurrently with iPhone 4S recordings and were reviewed by 2 trained and blinded physician reviewers (Drs. McManus and Mathias) to determine AF or NSR. Real-time rhythm analysis was conducted combining 3 statistical methods [(Root Mean Square of Successive RR Differences (RMSSD); Shannon Entropy (ShE); and Turning Point Ratio (TPR)] for rhythm analysis. Using established threshold values for these methods (8), the sensitivity, specificity, and predictive accuracy of RMSSD, ShE, and TPR for the detection of AF as compared to 12-lead electrocardiograms was examined. It has been found that RMSSD, ShE, and TPR were significantly lower in participants in AF compared with sinus rhythm. The 3 methods were inversely related to AF in regression models adjusting for key factors including heart rate and blood pressure which was measured with a blood pressure cuff during the patient's visit to UMASS Medical Center ($\beta$ coefficients per standard deviation increment in RMSSD, ShE, and TPR were −0.20, −0.35, −0.18; p for all was <0.001). An algorithm combining the 3 statistical methods demonstrated excellent sensitivity (0.99), specificity (0.97), and accuracy (0.98) for beat-to-beat discrimination of AF from normal sinus rhythm.

Motion and Noise Artifact Determination: The current prototype AF application, shown in FIG. 8, utilizes the smartphone's internal triaxial accelerometers to determine the most appropriate contact pressure on the smartphone's camera so that the best signal quality is obtained. It has been found that if a subject presses a finger onto the camera too hard or too lightly, the signal quality becomes poor. Hence, the triaxial accelerometers are used to provide instant feedback to the subject to use appropriate contact pressure on the smartphone's camera lens. Only when a good signal quality is quantitatively determined using a statistical measure known as the kurtosis value from each of the three accelerometers, is start data collection started. Derivation of the threshold value of kurtosis which signifies the presence of motion and noise artifacts is derived from a previous study (Selvaraj N, Mendelson Y, Shelley K H, Silverman D G, Chon K H. Statistical approach for the detection of motion/noise artifacts in Photoplethysmogram. Conf Proc IEEE Eng Med Biol Soc. 2011; 2011:4972-5, which is incorporated by reference herein in its entirety and for all purposes). During the first minute of recording, if the AF application determines that motion and noise artifacts were detected in more than three separate instances, then the data collection terminates and the application restarts the data collection from the beginning. The reason for this is to reduce false positive detection of AF as it is our experience that more than 3 episodes of motion and noise artifacts can lead to incorrect detection of AF.

The data on 95 subjects, shown in Table 3, are part of the on-going iPhone 4s study, which consists of taking data both pre- and post-cardioversion, performed at the University of Massachusetts Medical Center (UMMC). For PVC and PAC identification, the results are based on only 3 subjects with PVC and 4 subjects with PAC. As shown in Table 3, when the AF detection algorithms (RMSSD, TPR and ShE) is combined with the Poincare plot and KL diversion methods, detection of PVC and PAC is 100% and discrimination between the two rhythms is nearly 97%. These promising results warrant further validation using a larger cohort of subjects with PVC and PAC. It should also be noted that the Poincare algorithm is computationally real-time realizable since Matlab (2012 version) code takes only 0.6 seconds to compute. This computational speed will be significantly faster when optimized and coded in either C or C++ language.

TABLE 3

Test characteristics of PVC and PAC detection and discrimination using statistical methods* on a sample of 95 subjects' data recorded using iPhone 4s (88 subjects with AF (pre-cardioversion) and NSR (post-cardioversion), 4 subjects with PAC and 3 subjects with PVC)

| | PVC | | | PAC | | |
|---|---|---|---|---|---|---|
| Algorithm | Sensitivity | Specificity | Accuracy | Sensitivity | Specificity | Accuracy |
| RMSSD + TPR + ShE + Poincare Plot + KL diversion | 1.0000 | 0.9670 | 0.9676 | 1.0000 | 0.9721 | 0.9730 |

*Test Characteristics of PVC/PAC Detection Statistical Methods Established using the threshold values of RMSDD = 0.1300, Shannon Entropy = 0.7913, Poincare Plot = 0.1.

In one or more embodiments, the system of these teachings for physiological parameter monitoring includes a physiological indicator signal sensing component (sensor) and a mobile communication device having an analysis component analyzing the physiological indicator signal to obtain measurements of one or more physiological parameters and a motion artifact detection component detecting effects of motion artifacts in the measurements of the one or more physiological parameters.

In one instance, the mobile communication device includes one or more processors and one or more computer usable media, where the computer usable media has computer readable code embodied therein that causes the processor to analyze the physiological indicator signal to obtain measurements of one or more physiological parameters and to detect effects of motion artifacts in the measurements of the one or more physiological parameters. In one or more embodiments, the computer readable code causes the processor to implement the methods described hereinabove.

It should be noted that other embodiments of the mobile communication device, such as the use of ASICs or FPGAs in order to implement the analysis component and/or the motion artifact detection component are within the scope of these teachings.

FIG. 7 is a block diagram representation of one embodiment of the system of these teachings. Referring to FIG. 7, in the embodiment shown therein, a mobile communication system 280 includes a processor 250 and one or more memories 260. A physiological indicator signal sensing component (sensor) 270 supplies a physiological indicators signal to the mobile communication device 280. The sensor 270 can be a photoplethysmographic (PPG) sensor or an electrocardiogram (EKG) sensor. In the embodiment shown in FIG. 8, a camera 265, where the camera as an objective lens 267, can also supply the physiological indicators signal to the mobile communication device 280. The one or more memories 260 have computer usable code embodied therein that causes the processor 250 to that causes the processor to analyze the physiological indicator signal to obtain measurements of one or more physiological parameters and to detect effects of motion artifacts in the measurements of the one or more physiological parameters. In one or more instances, the computer readable code causes the processor 250 to perform the implement the methods described hereinabove.

The one or more memories 260 represent one embodiment of computer usable media having computer readable code embodied therein that causes a processor to implement the methods of these teachings. Embodiments of the method of these teachings are described hereinabove and the computer readable code can cause a processor to implement those embodiments.

In the embodiment shown in FIG. 7, the mobile communication device 280 also includes an antenna 265 that enables communications through one or more of a variety of wireless protocols or over wireless networks. It should be noted that, although the sensor 270 is shown as being directly connected to the mobile communication device 280, embodiments in which the sensor 270 provides the physiological indicators signal to the mobile communication device 280 through a wireless connection are also within the scope of these teachings.

In one embodiment, the mobile communication device 280 also includes internal triaxial accelerometers that are used to determine good signal quality by using a statistical measure known as the kurtosis value from each of the three accelerometers.

The following is a disclosure by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hardwired or customized circuitry to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive or external to the computing device, such as a remote memory, a disc farm or other mass storage device, etc. Commercially available microprocessors, one or more of which could be a computing device or part of a computing device, include a PA-RISC series microprocessor from Hewlett-Packard Company, an 80×86 or Pentium series microprocessor from Intel Corporation, a PowerPC microprocessor from IBM, a Spare microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The inter-connect may include one or more buses connected to one another through various bridges, controllers and/or adapters. In one embodiment the I/O controller includes a USB (Universal Serial Bus) adapter for controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile ROM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD ROM, a DVD or a CD), or 'other type of memory system which maintains data even after power is removed from the system.

A server could be made up of one or more computing devices. Servers can be utilized, e.g., in a network to host a network database, compute necessary variables and information from information in the database(s), store and recover information from the database(s), track information and variables, provide interfaces for uploading and downloading information and variables, and/or sort or otherwise manipulate information and data from the database(s). In one embodiment a server can be used in conjunction with other computing devices positioned locally or remotely to perform certain calculations and other functions as may be mentioned in the present application.

At least some aspects of the disclosed subject matter can be embodied, at least in part, utilizing programmed software code/instructions. That is, the functions, functionalities and/or operations techniques may be carried out in a computing device or other data processing system in response to its processor, such as a microprocessor, executing sequences of instructions contained in a memory, such as ROM, volatile RAM, non-volatile memory, cache or a remote storage device. In general, the routines executed to implement the embodiments of the disclosed subject matter may be implemented as part of an operating system or a specific application, component, program, object, module or sequence of instructions usually referred to as "computer programs," or "software." The computer programs typically comprise instructions stored at various times in various tangible memory and storage devices in a computing device, such as in cache memory, main memory, internal or external disk drives, and other remote storage devices, such as a disc farm, and when read and executed by a processor(s) in the computing device, cause the computing device to perform a method(s), e.g., process and operation steps to execute an element(s) as part of some aspect(s) of the method(s) of the disclosed subject matter.

A tangible machine readable medium can be used to store software and data that, when executed by a computing device, causes the computing device to perform a method(s) as may be recited in one or more accompanying claims defining the disclosed subject matter. The tangible machine readable medium may include storage of the executable software program code/instructions and data in various tangible locations, including for example ROM, volatile RAM, non-volatile memory and/or cache. Portions of this program software code/instructions and/or data may be stored in any one of these storage devices. Further, the program software code/instructions can be obtained from remote storage, including, e.g., through centralized servers or peer to peer networks and the like. Different portions of the software program code/instructions and data can be obtained at different times and in different communication sessions or in a same communication session.

The software program code/instructions and data can be obtained in their entirety prior to the execution of a respective software application by the computing device. Alternatively, portions of the software program code/instructions and data can be obtained dynamically, e.g., just in time, when needed for execution. Alternatively, some combination of these ways of obtaining the software program code/instructions and data may occur, e.g., for different applications, components, programs, objects, modules, routines or other sequences of instructions or organization of sequences of instructions, by way of example. Thus, it is not required that the data and instructions be on a single machine readable medium in entirety at any particular instance of time.

In general, a tangible machine readable medium includes any tangible mechanism that provides (i.e., stores) information in a form accessible by a machine (i.e., a computing device, which may be included, e.g., in a communication device, a network device, a personal digital assistant, a mobile communication device, whether or not able to download and run applications from the communication network, such as the Internet, e.g., an I-phone, Blackberry, Droid or the like, a manufacturing tool, or any other device including a computing device, comprising one or more data processors, etc.

Although these teachings have been described with respect to various embodiments, it should be realized these teachings is also capable of a wide variety of further and other embodiments within the spirit and scope of the appended claims.

What is claimed is:

1. A computer implemented method for discriminating between atrial fibrillation and premature ventricular contractions (PVC) and premature atrial contractions (PACs), the method comprising:
   demarcating boundaries in a Poincare plot space, the boundaries being obtained from data from a test set of test subjects; the Poincare plot space being a space of time interval between consecutive pulses obtained by sensing variability in heart rate signal;
   constructing a Poincare plot of time interval data from a subject under test; the time interval being a time interval between consecutive pulses obtained by sensing variability in heart rate signal from the subject under test;
   identifying data in patterns in the Poincare plot, the patterns including patterns corresponding to combinations of at least one of bigeminy, trigemini, and quadragemini indicating one of PAC or PVC;
   obtaining updated data by subtracting the data in the patterns corresponding to combinations of at least one of bigeminy, trigemini, quadragemini indicating one of PAC or PVC from the time interval data from the subject under test;
   obtaining a root mean squared of successive differences, a Shannon entropy and a turning point ratio for the updated data;
   comparing the root mean square of successive differences to a first predetermined threshold; comparing the Shannon entropy to a second predetermined threshold;
   comparing the turning point ratio to a third predetermined threshold;
   determining, if each of the root mean square of successive differences, the Shannon entropy, and the turning point ratio is not less than a corresponding predetermined threshold, that the subject under test has atrial fibrillation; and
   determining, if each of the root mean square of successive differences, the Shannon entropy, and the turning point ratio is less than a corresponding predetermined threshold, that the subject under test has normal sinus rhythm (NSR) with PVC or PAC;
   wherein demarcating boundaries in a Poincare plot space, constructing a Poincare plot, identifying data in patterns in the Poincare plot, obtain updated data, obtaining root mean squared of successive differences, Shannon entropy and turning point ratio for the updated data, comparing to predetermined thresholds, and determining whether the subject under test has atrial fibrillation or the subject under test has normal sinus rhythm (NSR) with PVC or PAC are performed by one or more processors executing computer readable code embodied in non-transitory computer usable media.

2. The computer implemented method of claim 1 wherein the determining that the subject under test has normal sinus rhythm (NSR) with PVC or PAC comprises:
   constructing a first probability distribution for peak amplitude data from the subject under test;
   obtaining a first Kullback-Leibler divergence for a second probability distribution and the first probability distribution; the second probability distribution being constructed from peak amplitude data for another test set of subjects with PAC;
   obtaining a second Kullback-Leibler divergence for a third probability distribution and the first probability distribution; the third probability distribution being constructed from peak amplitude data for yet another test set of subjects with PVC;
   determining that the subject under test has NSR with PAC if the first Kullback-Leibler divergence is greater than the second Kullback-Leibler divergence; and
   determining that the subject under test has NSR with PVC if the first Kullback-Leibler divergence is at most equal to the second Kullback-Leibler divergence.

3. The computer implemented method of claim 2 further comprising determining whether a PAC or PVC pattern is quadrigeminy pattern, by:
   identifying whether repeating pulse interval patterns are "short-short-long-short-short" (SSLSS) patterns;
   determining a number of turning points in identified SSLSS patterns;
   determining an expected number of turning points by a predetermined relation; comparing a difference between the number of turning points and the expected number of turning points to a fourth predetermined threshold; and
   determining, if the difference is greater than the fourth predetermined threshold, that the PAC or PVC pattern is a quadrigeminy pattern.

4. The computer implemented method of claim 2 further comprising determining whether a PAC or PVC pattern is trigeminy pattern, by:
   identifying whether repeating pulse interval patterns are "short-long short" (SLS) or "long-short-long" (LSL) patterns;
   determining a number of turning points in identified patterns;

determining an expected number of turning points by a predetermined relation; comparing a difference between the number of turning points and the expected number of turning points to a fourth predetermined threshold; and determining, if the difference is greater than the fourth predetermined threshold, that the PAC or PVC pattern is a trigeminy pattern.

5. The computer implemented method of claim 1 further comprising:

obtaining, before demarcating boundaries in the Poincare plot space, a second root mean square of successive differences, a second Shannon entropy and a second turning point ratio for the time interval data from a subject under test;

comparing the second root mean square of successive differences to a fourth predetermined threshold;

comparing the second Shannon entropy to a fifth predetermined threshold;

comparing the second turning point ratio to a sixth predetermined threshold;

determining, if each of the second root mean square of successive differences, the second Shannon entropy, and the second turning point ratio is less than a corresponding predetermined threshold, that the subject under test exhibits NSR without PAC or PVC; and ending, if the subject under test exhibits NSR without PAC or PVC, the computer implemented method.

6. The computer implemented method of claim 1 wherein the heart rate signal from the subject under test is obtained using a handheld mobile communication device.

7. The computer implemented method of claim 6 wherein sensing variability in heart rate signal from the subject under test comprises:

detecting signal from triaxial accelerometers in the handheld mobile communication device;

obtaining a kurtosis value for a signal from each triaxial accelerometer;

comparing the kurtosis value for the signal for each triaxial accelerometer to a predetermined threshold;

acquiring the heart rate signal from the subject under test, only if the kurtosis value for each accelerometer is at most equal to the predetermined threshold.

8. A system for discriminating between atrial fibrillation and premature ventricular contractions (PVC) and premature atrial contractions (PACs), the system comprising:

one or more processors; and computer usable media having computer readable code embodied therein that, when executed in the one or more processors, causes the one or more processors to:

demarcate boundaries in a Poincare plot space, the boundaries being obtained from data from a test set of test subjects; the Poincare plot space being a space of time interval between consecutive pulses obtained by sensing variability in heart rate signal;

construct a Poincare plot of time interval data from a subject under test; the time interval being a time interval between consecutive pulses obtained by sensing variability in heart rate signal from the subject under test;

identify data in patterns in the Poincare plot, the patterns including patterns corresponding to combinations of at least one of bigeminy, trigemini, and quadragemini indicating one of PAC or PVC;

obtain updated data by subtracting the data in the patterns corresponding to combinations of at least one of bigeminy, trigemini, quadragemini indicating one of PAC or PVC from the time interval data from the subject under test;

obtain root mean squared of successive differences, Shannon entropy and turning point ratio for the updated data;

compare the root mean square of successive differences to a first predetermined threshold; comparing the Shannon entropy to a second predetermined threshold;

compare the turning point ratio to a third predetermined threshold;

determine, if each of the root mean square of successive differences, the Shannon entropy, and the turning point ratio is not less than a corresponding predetermined threshold, the subject under test has atrial fibrillation; and determine if each of the root mean square of successive differences, the Shannon entropy, and the turning point ratio is less than a corresponding predetermined threshold, that the subject under test has normal sinus rhythm (NSR) with PVC or PAC.

9. The system of claim 8 wherein the computer readable code, when executed in the one or more processors, further causes the one or more processors to:

construct a first probability distribution for peak amplitude data from the subject under test;

obtain a first Kullback-Leibler divergence for a second probability distribution and the first probability distribution; the second probability distribution being constructed from peak amplitude data for another test set of subjects with PAC;

obtain a second Kullback-Leibler divergence for a third probability distribution and the first probability distribution; the third probability distribution being constructed from peak amplitude data for another test set of subjects with PVC;

determine that the subject under test has NSR with PAC if the first Kullback-Leibler divergence is greater than the second Kullback-Leibler divergence; and determine that the subject under test has NSR with PVC if the first Kullback-Leibler divergence is at most equal to the second Kullback-Leibler divergence.

10. The system of claim 9 wherein the computer readable code, when executed in the one or more processors, further causes the one or more processors to:

determine whether a PAC or PVC pattern is quadrigeminy pattern, by:

identifying whether repeating pulse interval patterns are "short-short-long-short-short" (SSLSS) patterns;

determining a number of turning points in identified SSLSS patterns;

determining an expected number of turning points by a predetermined relation;

comparing a difference between the number of turning points and the expected number of turning points to a fourth predetermined threshold; and determining, if the difference is greater than the fourth predetermined threshold, that the PAC or PVC pattern is a quadrigeminy pattern.

11. The system of claim 9 wherein the computer readable code, when executed in the one or more processors, further causes the one or more processors to:

determine whether a PAC or PVC pattern is trigeminy pattern, by:

identifying whether repeating pulse interval patterns are "short-long short" (SLS) or "long-short-long" (LSL) patterns;

determining a number of turning points in identified patterns;

determining an expected number of turning points by a predetermined relation;

comparing a difference between the number of turning points and the expected number of turning points to a fourth predetermined threshold; and determining, if the difference is greater than the fourth predetermined threshold, that the PAC or PVC pattern is a trigeminy pattern.

12. The system of claim 8 wherein the computer readable code, when executed in the one or more processors, further causes the one or more processors to:

obtain, before demarcating boundaries in the Poincare plot space, a second root mean square of successive differences, a second Shannon entropy and a second turning point ratio for the time interval data from a subject under test;

compare the second root mean square of successive differences to a fourth predetermined threshold;

compare the second Shannon entropy to a fifth predetermined threshold;

compare the second turning point ratio to a six predetermined threshold;

determine, if each of the second root mean square of successive differences, the second Shannon entropy, and the second turning point ratio is less than a corresponding predetermined threshold, that the subject under test exhibits NSR without PAC or PVC; and end, when the subject under test exhibits NSR without PAC or PVC, execution of the computer readable code.

13. The system of claim 8 wherein the one or more processors and the computer usable media are incorporated in a handheld mobile communication device.

14. The system of claim 13 further comprising:

an image acquisition component incorporated in the handheld mobile communication device, the pulses obtained by sensing variability in heart rate signal from the subject under test being obtained using the image acquisition component.

15. The system of claim 14 further comprising:

triaxial accelerometers incorporated in the handheld mobile communication device; and wherein the computer readable code, when executed in the one or more processors, further causes the one or more processors to:

detect signals from triaxial accelerometers in the handheld mobile communication device;

obtain a kurtosis value for a signal from each triaxial accelerometer;

compare the kurtosis value for the signal for each triaxial accelerometer to a predetermined threshold; and acquire the heart rate signal from the subject under test, only if the kurtosis value for each accelerometer is at most equal to the predetermined threshold.

16. A non-transitory computer usable medium having computer readable code embodied therein, the computer readable code, when executed in one or more processors, causing the one or more processors to:

demarcate boundaries in a Poincare plot space, the boundaries being obtained from data from a test set of test subjects; the Poincare plot space being a space of time interval between consecutive pulses obtained by sensing variability in heart rate signal;

construct a Poincare plot of time interval data from a subject under test; the time interval being a time interval between consecutive pulses obtained by sensing variability in heart rate signal from the subject under test;

identify data in patterns in the Poincare plot, the patterns including patterns corresponding to combinations of at least one of bigeminy, trigemini, and quadragemini indicating one of PAC or PVC;

obtain updated data by subtracting the data in the patterns corresponding to combinations of at least one of bigeminy, trigemini, quadragemini indicating one of PAC or PVC from the time interval data from the subject under test;

obtain a root mean squared of successive differences, a Shannon entropy and a turning point ratio for the updated data;

compare the root mean square of successive differences to a first predetermined threshold; comparing the Shannon entropy to a second predetermined threshold; and compare the turning point ratio to a third predetermined threshold;

determine, if each of the root mean square of successive differences, the Shannon entropy, and the turning point ratio is not less than a corresponding predetermined threshold, the subject under test has atrial fibrillation; and determine, if each of the root mean square of successive differences, the Shannon entropy, and the turning point ratio is less than at least equal to a corresponding predetermined threshold, that the subject under test has normal sinus rhythm (NSR) with PVC or PAC.

17. The non-transitory computer usable medium of claim 16 wherein the computer readable code, when executed in the one or more processors, further causes the one or more processors to:

construct a first probability distribution for peak amplitude data from the subject under test;

obtain a first Kullback-Leibler divergence for a second probability distribution and the first probability distribution; the second probability distribution being constructed from peak amplitude data for another test set of subjects with PAC;

obtain a second Kullback-Leibler divergence for a third probability distribution and the first probability distribution; the third probability distribution being constructed from peak amplitude data for yet another test set of subjects with PVC;

determine that the subject under test has NSR with PAC if the first Kullback-Leibler divergence is greater than the second Kullback-Leibler divergence; and determine that the subject under test has NSR with PVC if the first Kullback-Leibler divergence is at most equal to the second Kullback-Leibler divergence.

18. The non-transitory computer usable medium of claim 17 wherein the computer readable code, when executed in the one or more processors, further causes the one or more processors to:

determine whether a PAC or PVC pattern is quadrigeminy pattern, by:

identifying whether repeating pulse interval patterns are "short-short-long-short-short" (SSLSS) patterns;

determining a number of turning points in identified SSLSS patterns;

determining an expected number of turning points by a predetermined relation; comparing a difference between the number of turning points and the expected number of turning points to a fourth predetermined threshold; and determining, if the difference is greater than the fourth predetermined threshold, that the PAC or PVC pattern is a quadrigeminy pattern.

19. The non-transitory computer usable medium of claim 17 wherein the computer readable code, when executed in the one or more processors, further causes the one or more processors to:

determine whether a PAC or PVC pattern is trigeminy pattern, by:

identifying whether repeating pulse interval patterns are "short-long short" (SLS) or "long-short-long" (LSL) patterns;

determining a number of turning points in identified patterns;

determining an expected number of turning points by a predetermined relation; comparing a difference between the number of turning points and the expected number of turning points to a fourth predetermined threshold; and determining, if the difference is greater than the fourth predetermined threshold, that the PAC or PVC pattern is a trigeminy pattern.

20. The non-transitory computer usable medium of claim 16 wherein the computer readable code, when executed in the one or more processors, further causes the one or more processors to:

obtain, before demarcating boundaries in the Poincare plot space, a second root mean square of successive differences, a second Shannon entropy and a second turning point ratio for the time interval data from a subject under test;

compare the second root mean square of successive differences to a fourth predetermined threshold;

compare the second Shannon entropy to a fifth predetermined threshold;

compare the second turning point ratio to a six predetermined threshold;

determine, if each of the second root mean square of successive differences, the second Shannon entropy, and the second turning point ratio is less than a corresponding predetermined threshold, that the subject under test exhibits NSR without PAC or PVC; and end, when the subject under test exhibits NSR without PAC or PVC, execution of the computer readable code.

\* \* \* \* \*